United States Patent
Morgan, III (12)

(10) Patent No.: US 10,976,201 B2
(45) Date of Patent: Apr. 13, 2021

(54) LIQUID COLOR, HAZE, AND CLARITY INSTRUMENT, AND METHOD OF MEASUREMENT

(71) Applicant: Ranzy Morgan, III, Galveston, TX (US)

(72) Inventor: Ranzy Morgan, III, Galveston, TX (US)

(*) Notice: Subject to any disclaimer, the term of this patent is extended or adjusted under 35 U.S.C. 154(b) by 0 days.

(21) Appl. No.: 16/396,287

(22) Filed: Apr. 26, 2019

(65) Prior Publication Data
US 2019/0391013 A1    Dec. 26, 2019

Related U.S. Application Data

(60) Provisional application No. 62/689,726, filed on Jun. 25, 2018, provisional application No. 62/745,187, filed on Oct. 12, 2018.

(51) Int. Cl.
| | | |
|---|---|---|
| *G01J 3/42* | (2006.01) | |
| *G01J 3/28* | (2006.01) | |
| *G01N 21/59* | (2006.01) | |
| *G01N 21/01* | (2006.01) | |

(Continued)

(52) U.S. Cl.
CPC ............... *G01J 3/42* (2013.01); *G01J 3/2803* (2013.01); *G01N 21/01* (2013.01); *G01N 21/59* (2013.01); *G01N 33/22* (2013.01); *G01N 33/2888* (2013.01)

(58) Field of Classification Search
None
See application file for complete search history.

(56) References Cited

U.S. PATENT DOCUMENTS 4,762,413 A * 8/1988 Namba ................ G01N 21/253
                                                        250/574
5,007,733 A * 4/1991 Laurent ............. G01N 33/2811
                                                         356/70

(Continued)

OTHER PUBLICATIONS

A Good Choice for Haze Determination Achieves ASTM D8148-17 Designation, Petro Industry News, Jan. 5, 2018, available at https://www.petro-online.com/news/analytical-instrumentation/11/choice-analytical/a-good-choice-for-haze-determination-achieves-astm-d8148-17-designation/44698, 2 Pages (p. 1, para 1; p. 2, para 2-3).

(Continued)

*Primary Examiner* — Shawn DeCenzo
(74) *Attorney, Agent, or Firm* — Alberto Q. Amatong, Jr.; Amatong McCoy LLC

(57) ABSTRACT

The present disclosure provides for an apparatus for measuring optical properties of liquid samples. The apparatus includes a sample chamber and a spectrometer optically coupled with the sample chamber. One or multiple sources of electromagnetic radiation are positioned relative to the sample chamber to direct electromagnetic radiation through the sample chamber to measure the color, haze, and/or clarity of the sample. Also provided is a method for measuring optical properties of liquid samples, including inserting a cuvette containing a liquid sample into the sample chamber of the apparatus, and directing electromagnetic radiation from the one or more sources and through the sample to measure the color, haze, and/or clarity of the sample. The apparatus and methods may be used to analyze various samples, such as petroleum-based fluids, including fuels and lubricants.

25 Claims, 14 Drawing Sheets

(51) Int. Cl.
*G01N 33/28* (2006.01)
*G01N 33/22* (2006.01)

(56) References Cited

U.S. PATENT DOCUMENTS

| | | | | |
|---|---|---|---|---|
| 5,825,478 A * | 10/1998 | Wilcox | ............ | G01J 3/36 |
| | | | | 356/73 |
| 6,825,921 B1 * | 11/2004 | Modlin | ............ | G01N 21/255 |
| | | | | 235/454 |
| 8,248,255 B2 | 8/2012 | Tzidon et al. | | |
| 9,041,920 B2 * | 5/2015 | Mander | ............ | G01N 21/01 |
| | | | | 356/51 |
| 9,448,112 B2 * | 9/2016 | Greer | ............ | G01N 21/33 |
| 9,869,636 B2 | 1/2018 | Mander et al. | | |
| 2002/0042142 A1 * | 4/2002 | Kawamura | ............ | G01N 21/82 |
| | | | | 436/50 |
| 2003/0058450 A1 * | 3/2003 | Mosley | ............ | G01N 21/534 |
| | | | | 356/436 |
| 2005/0095716 A1 * | 5/2005 | Wollenberg | ............ | C10M 171/00 |
| | | | | 436/60 |
| 2009/0098022 A1 * | 4/2009 | Tokhtuev | ............ | G01N 21/274 |
| | | | | 422/82.05 |
| 2010/0202726 A1 | 8/2010 | Egalon | | |
| 2011/0255745 A1 | 10/2011 | Hodder et al. | | |
| 2014/0233015 A1 * | 8/2014 | Mander | ............ | G01N 21/0303 |
| | | | | 356/51 |
| 2014/0234952 A1 * | 8/2014 | Moore | ............ | G01N 21/6486 |
| | | | | 435/288.7 |
| 2015/0260641 A1 * | 9/2015 | Sperling | ............ | G01N 21/474 |
| | | | | 356/72 |
| 2015/0276594 A1 * | 10/2015 | Johnson | ............ | G01N 21/51 |
| | | | | 356/338 |
| 2016/0040985 A1 * | 2/2016 | Nagai | ............ | G01N 21/8422 |
| | | | | 356/328 |
| 2017/0199079 A1 * | 7/2017 | Takebe | ............ | G01N 21/57 |
| 2018/0059006 A1 * | 3/2018 | Fritchie | ............ | G01N 33/483 |
| 2019/0310193 A1 * | 10/2019 | Scardina | ............ | G01N 21/251 |
| 2020/0132593 A1 * | 4/2020 | Schwarz | ............ | G01J 3/524 |
| 2020/0209208 A1 * | 7/2020 | Li | ............ | G01N 21/31 |

OTHER PUBLICATIONS

International Search Report and Written Opinion dated Jul. 26, 2019 (issued in PCT Application No. PCT/US2019/029403) [15 pages].

* cited by examiner

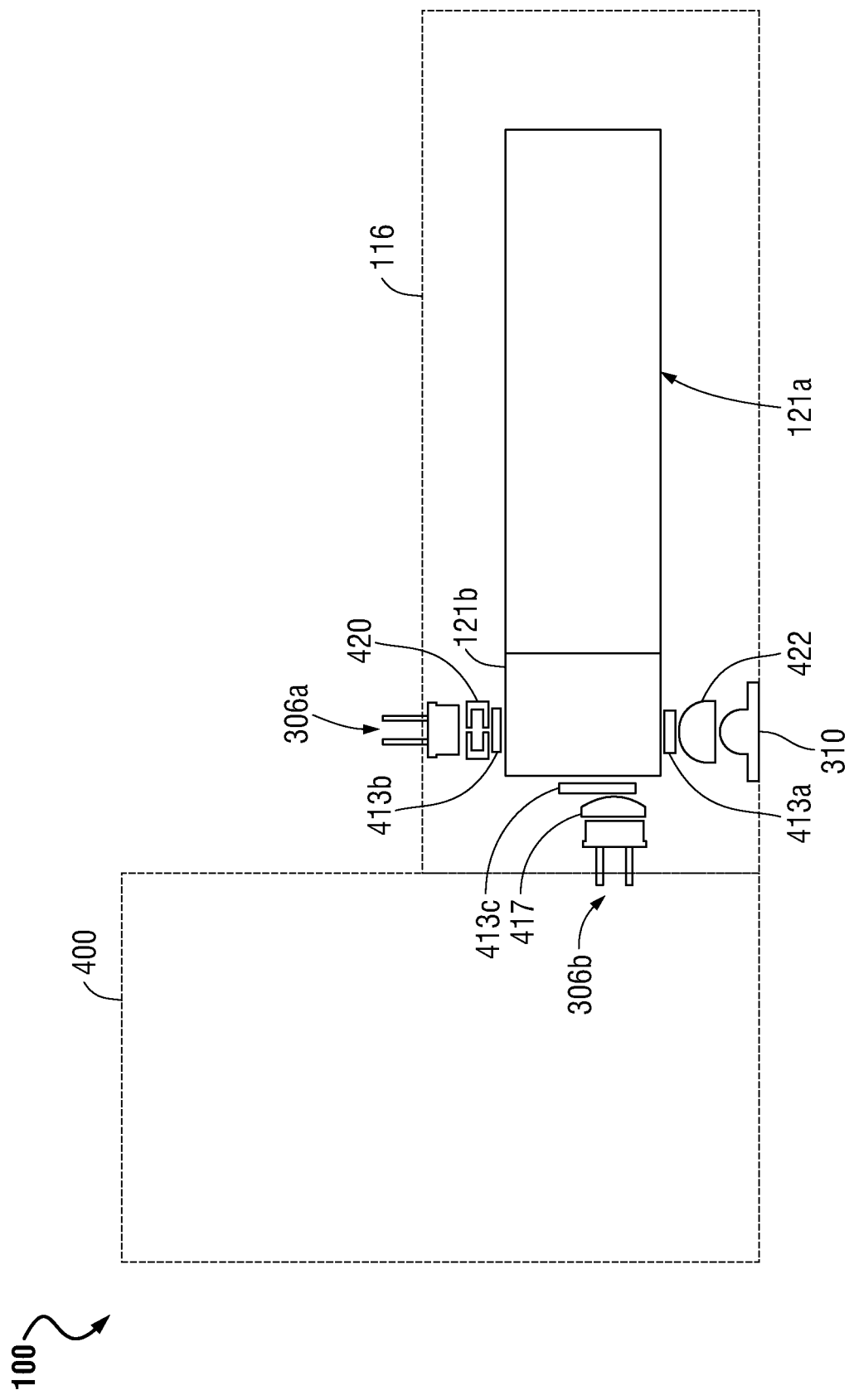

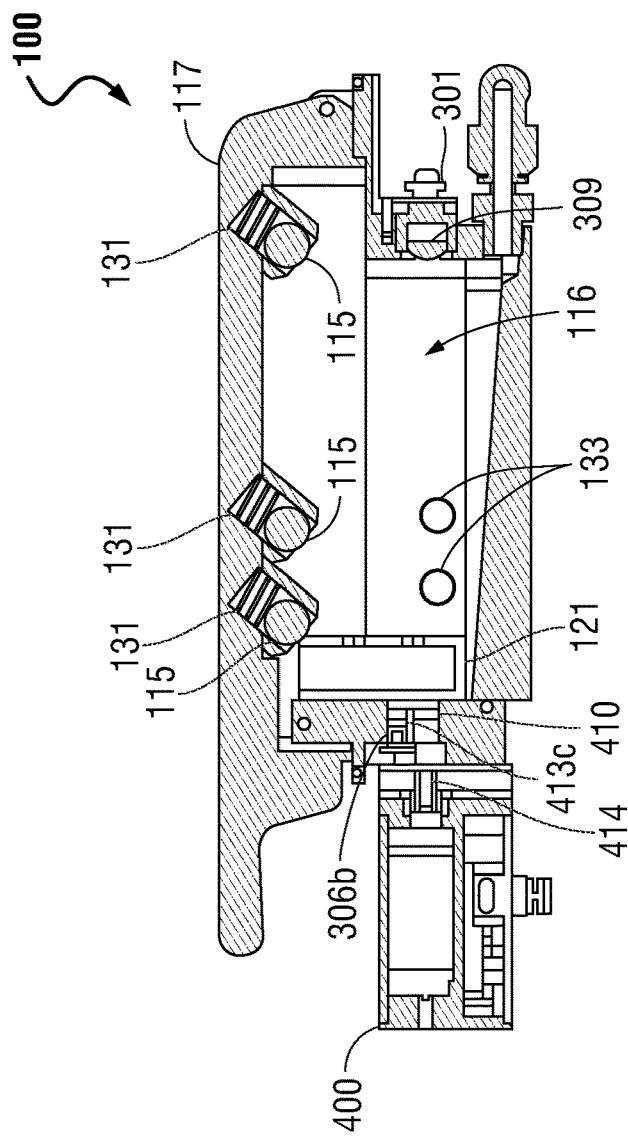
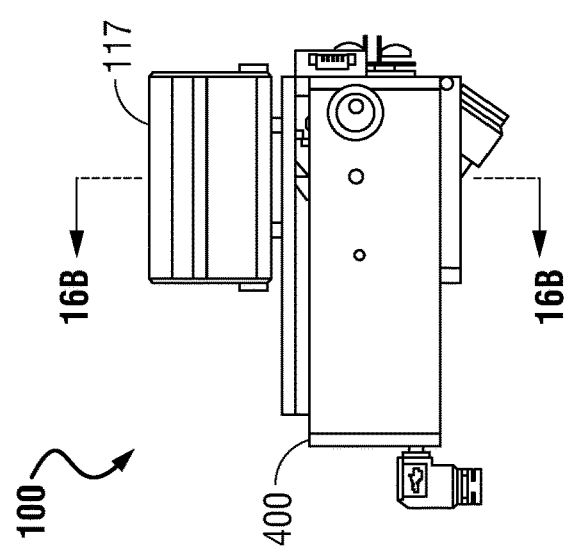
FIG. 16B
FIG. 16A

US 10,976,201 B2

LIQUID COLOR, HAZE, AND CLARITY INSTRUMENT, AND METHOD OF MEASUREMENT

CROSS-REFERENCE TO RELATED APPLICATIONS

The present application claims the benefit of U.S. Provisional Patent Application No. 62/689,726, filed on Jun. 25, 2018, and entitled "LIQUID COLOR, HAZE, AND CLARITY INSTRUMENT, AND METHOD OF MEASUREMENT", the entirety of which is incorporated herein by reference. The present application also claims the benefit of U.S. Provisional Patent Application No. 62/745,187, filed on Oct. 12, 2018, and entitled "LIQUID COLOR, HAZE, AND CLARITY INSTRUMENT, AND METHOD OF MEASUREMENT", the entirety of which is incorporated herein by reference.

FIELD

The present application relates to instrumentation, apparatus and systems for measuring properties of liquids, as well as to methods of making and using the same.

BACKGROUND

Optical properties of fuels are typically mandated to meet certain specifications, such as certain clarity and brightness specifications. The determination of optical properties, such as haze, clarity, and color allows the quality of petroleum-based fluids, such as fuels and lubricants, to be assessed. Typically, such properties are determined by multiple, different instruments using multiple, different tests, including subjective techniques. For example, the determination of haze in fuels has typically involved the use of subjective, visual techniques, such as that defined by ASTM D4176, Procedure 2. The degree of specificity and detail about the fuel properties, such as clarity and quality, that are determined by such techniques is limited.

Cloudiness and/or haziness in a fuel, which may be caused by the presence of suspended solid particulates and/or water within the fuel, can lead to the fuel not meeting the required optical specifications. It would be desirable to have instrumentation, apparatus, systems, and methods for objectively measuring such optical properties of liquids that is not reliant upon subjective visual techniques, which vary with operator and lighting conditions.

Prior haze measuring instruments only take either pure transmission measurements or pure scattering measurements, providing measurement results that are either percent transmission or relative scatter. Such measurement results, alone, are of little to no value to the fuels and lubricants industry. Further, such measurement results can be inconsistent, unreliable, and erratic (in both transmission and scatter measurements) when samples are opaque due to particulates or other contaminants.

SUMMARY

One aspect of the present disclosure includes an apparatus for measuring optical properties of liquid samples. The apparatus includes a sample chamber, and a spectrometer optically coupled with the sample chamber. A first source of electromagnetic radiation is positioned relative to the sample chamber to direct electromagnetic radiation through the sample chamber along an optical path for measurement of color. A second source of electromagnetic radiation is positioned relative to the sample chamber to direct electromagnetic radiation through the sample chamber along an optical path for measurement of haze. A first photodetector is optically coupled with the sample chamber, and a second photodetector is optically coupled with the sample chamber. The first photodetector and the second source of electromagnetic radiation are positioned relative to one another and to the sample chamber to define a first detection channel along which electromagnetic radiation from the second source of electromagnetic radiation passes through the sample chamber into the first photodetector to measure transmittance of the electromagnetic radiation through the sample chamber. The second photodetector and the second source of electromagnetic radiation are positioned relative to one another and to the sample chamber to define a second detection channel along which electromagnetic radiation from the second source of electromagnetic radiation is scattered within the sample chamber and into the second photodetector to measure scatter of the electromagnetic radiation within the sample chamber.

Another embodiment of the present disclosure relates to a method for measuring optical properties of liquid samples. The method includes inserting a cuvette containing a first sample of a liquid into a sample chamber of an apparatus, and directing electromagnetic radiation through the first sample and to a spectrometer to measure a color of the liquid. The method includes inserting a cuvette containing a second sample of the liquid into the sample chamber of the apparatus, and directing electromagnetic radiation through the second sample and to photodetectors to measure a haze of the liquid. The method may be implemented using the apparatus disclosed herein.

Other embodiments include liquids measured in accordance with the methods and using the apparatus disclosed herein.

BRIEF DESCRIPTION OF THE DRAWINGS

So that the manner in which the features and advantages of the systems, apparatus, products, and/or methods of the present disclosure may be understood in more detail, a more particular description briefly summarized above may be had by reference to the embodiments thereof which are illustrated in the appended drawings that form a part of this specification. It is to be noted, however, that the drawings illustrate only various exemplary embodiments and are therefore not to be considered limiting of the disclosed concepts as it may include other effective embodiments as well.

FIG. 15 is a simplified schematic of the apparatus of FIG. 12 showing features associated with haze and clarity measurement;

FIG. 16A is another view of an exemplary analyzer or measurement instrument;

FIG. 16B is a cross-sectional view along line A-A of FIG. 16A, showing the self-alignment features and sensors of the instrument;

Figure 1:
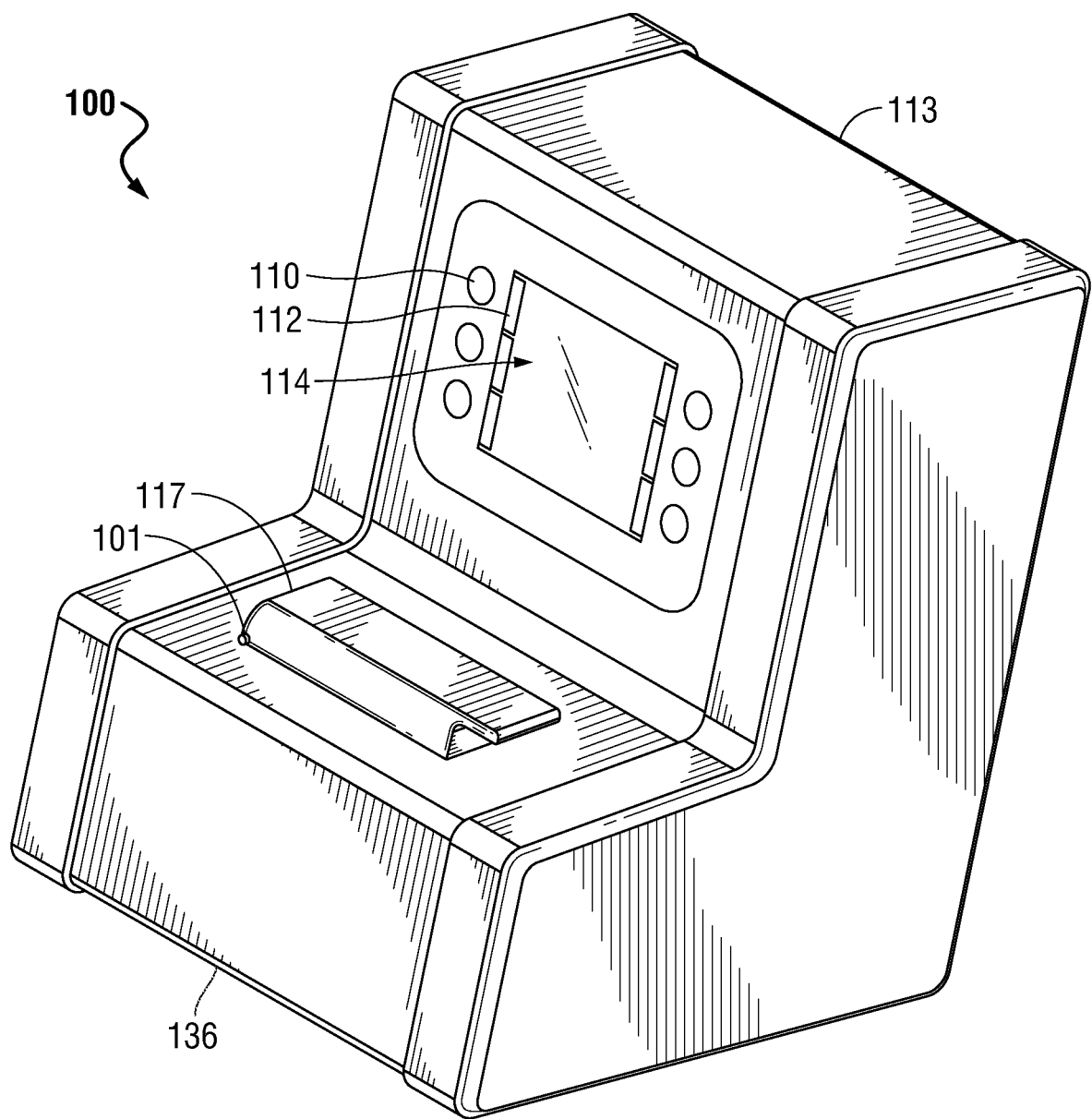
FIG. 1 is a perspective view of an exemplary analyzer or measurement instrument, according to the present disclosure.
Figure 2:
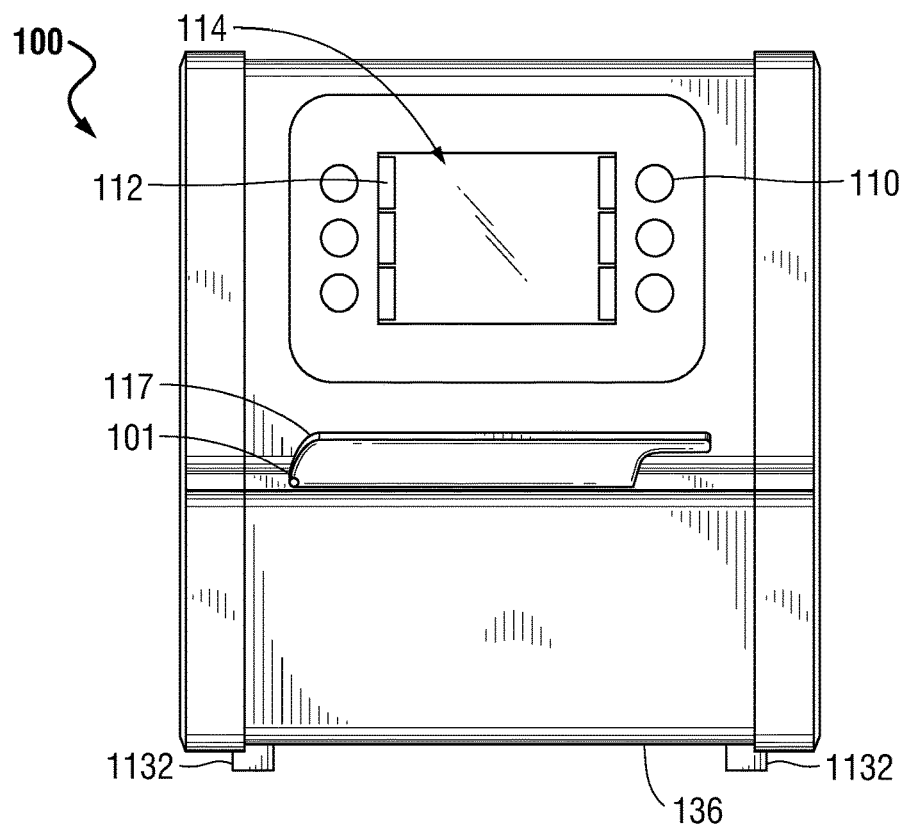
FIG. 2 is a front view of the apparatus of FIG. 1.
Figure 3:
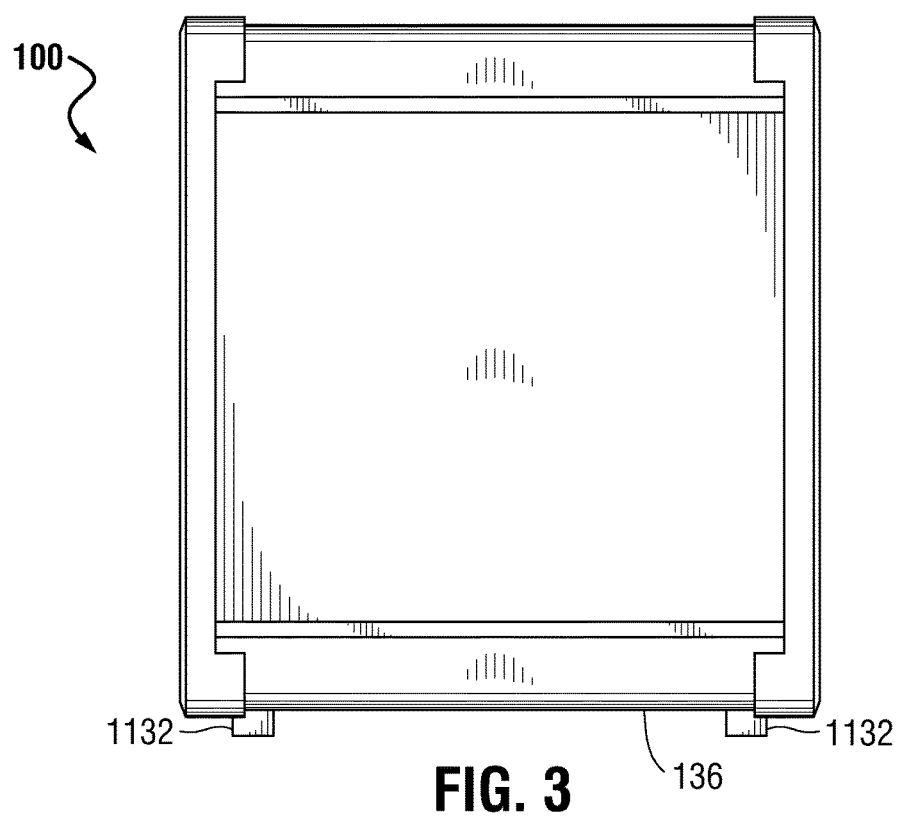
FIG. 3 is a rear view of the apparatus of FIG. 1.
Figure 4:
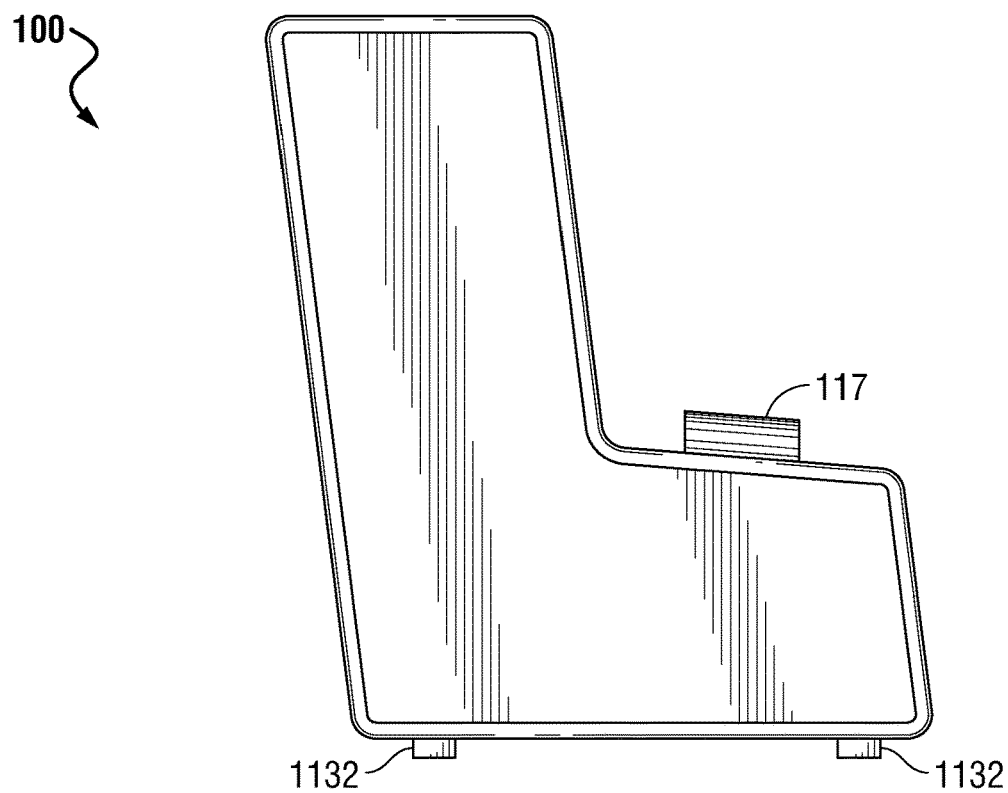
FIG. 4 is a first side view of the apparatus of FIG. 1.
Figure 5:
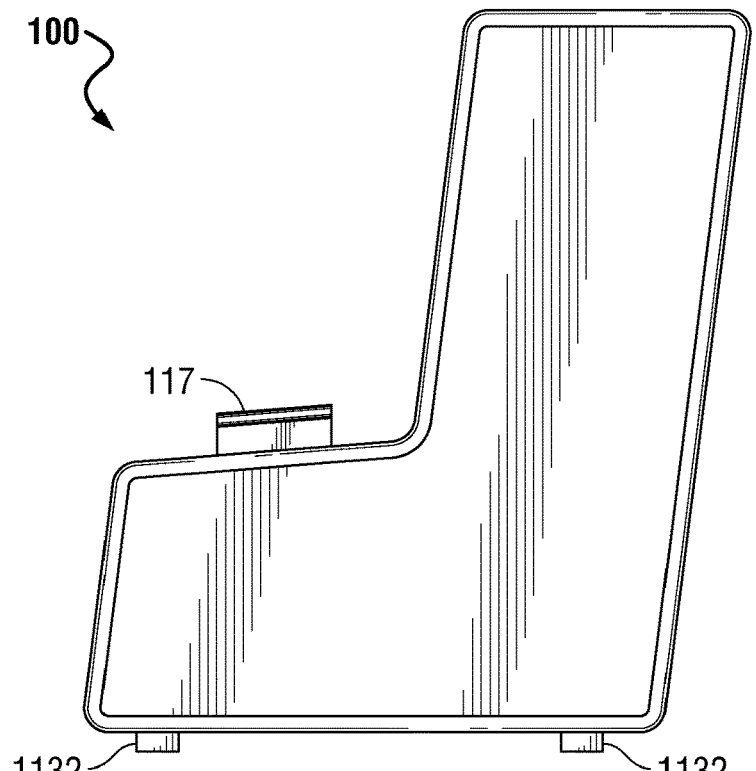
FIG. 5 is a second side view of the apparatus of FIG. 1.
Figure 6:
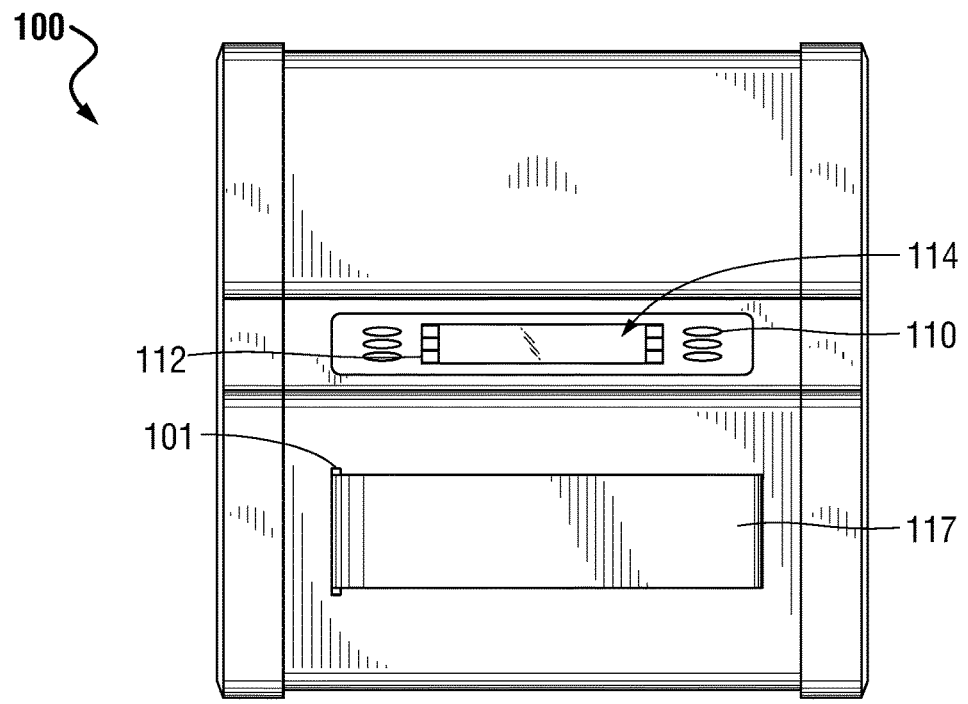
FIG. 6 is a top view of the apparatus of FIG. 1.
Figure 7:
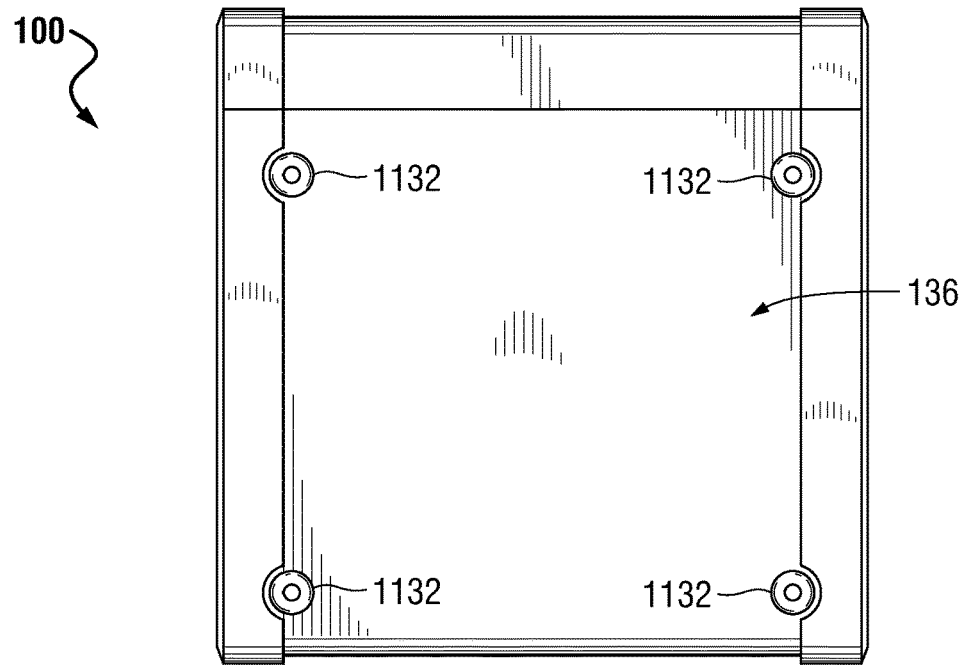
FIG. 7 is a bottom view of the apparatus of FIG. 1.

Products, apparatus, systems and methods according to present disclosure will now be described more fully with reference to the accompanying drawings, which illustrate various exemplary embodiments. Concepts according to the present disclosure may, however, be embodied in many different forms and should not be construed as being limited by the illustrated embodiments set forth herein. Rather, these embodiments are provided so that this disclosure will be thorough as well as complete and will fully convey the scope of the various concepts to those skilled in the art and the best and preferred modes of practice.

DETAILED DESCRIPTION

The present disclosure relates to systems, apparatus, instrumentation, and methods for analyzing liquids.

Liquids and Contaminates

The liquids analyzed in accordance with the present disclosure include, but are not limited to, petroleum-based liquids, such as petroleum-based fuels and petroleum-based lubricants. Some exemplary petroleum-based liquids that may be analyzed in accordance with the present disclosure include, but are not limited to, liquid middle distillate fuels, including those blended with synthesized hydrocarbons or biofuels. Such liquid middle distillate fuels include refinery products in the middle distillation range of refined products, such as heating oil, distillate fuel oil, gas oil, lighting oil, and cooking oil. Some examples of liquid middle distillate fuels include kerosene, jet fuel, diesel fuel, and marine bunker fuel. Liquid middle distillate fuels include fuels having from approximately eleven (11) to approximately eighteen (18) carbons present in each molecule thereof.

In certain aspects, the liquids analyzed in accordance with the present disclosure include contaminate contained (e.g., suspended) therein. The contaminate may include water, solid particulates, or combinations thereof.

Measurement Standards and Definitions

As used herein, "ASTM" refers to the American Society for Testing and Materials.

As used herein, "BIT" refers to a Built-in Test. A built-in test is a test procedure, including data collection and analysis procedures, that may be pre-installed onto the apparatus disclosed herein, such as in the form of software, including computer instructions, such computer executable algorithms.

Haze (transmission haze) is a measure of the amount of light that is diffused or scattered when passing through a material. As would be understood by one skilled in the art, "transmission" through a liquid sample refers to the amount of light that passes through the liquid sample without being scattered; "haze" refers to the amount of light that is subject to wide angle scattering (e.g., at an angle greater than 2.5° from normal (ASTM D1003)); and "clarity" refers to the amount of light that is subject to narrow area scattering (e.g., at an angle less than 2.5° from normal). In some aspects, "haze", as used herein, is measured in accordance with: ASTM D8148-17, Standard Test Method for Spectroscopic Determination of Haze in Fuels. In such aspects, the liquid is analyzed using spectroscopy to determine the level of suspended water and particulate contamination present therein. Such testing results in the determination of an ordinal, whole-number, Instrument Haze Rating (IHR) of from 1 to 6 and a Haze Clarity Index (HCI) of from 50.0 to 100.0 for a test specimen that is at a specified temperature or range, such as 22.0° C.±2.0° C.

As used herein, the "HCI" is a numerical value of from 50.0 to 100.0 that indicates fuel clarity derived from spectroscopic measurements and an algorithm that processes the spectroscopic measurements. The HCI values increase with sample clarity and range from 100.0 HCI for a relatively clear and bright sample to 50.0 HCI for a relatively cloudy and opaque sample. For example, a fuel with an HCI value of 90 has less haze than a fuel with an HCI value of 80. HCI can be used to evaluate haze intensity changes within a given IHR. In accordance with ASTM D4175, Haze Clarity Index (HCI) is an empirical definition of the haze of a middle distillate fuel based on a scale of 50 to 100 as determined by ASTM Test Method D8148. In accordance with ASTM D4176, Haze Clarity Index (HCI) is an empirical definition used to estimate the presence of suspended free water and solid particulate contamination in distillate fuels by generating a numerical value from 50.0 to 100.0 as determined by Test Method D8148.

As used herein, the IHR is an ordinal, whole number of from 1 to 6 that corresponds to haze ratings defined in ASTM Test Method D4176—Procedure 2, and is assigned to a test specimen based upon spectroscopic measurements and an algorithm that processes the spectroscopic measurements.

The determination of the color of petroleum products may be used for manufacturing control purposes and provides an indication of the quality characteristics of the liquid, as color is readily observed by the user of the product. In some cases, color may serve as an indication of the degree of refinement of the material. In some aspects, "color", as used herein, is measured in accordance with any of the following standards: ASTM D156-15, Standard Test Method for Saybolt Color of Petroleum Products (Saybolt Chromometer Method); ASTM D1500-12(2017), Standard Test Method for ASTM Color of Petroleum Products (ASTM Color Scale); ASTM D6045-12(2017), Standard Test Method for Color of Petroleum Products by the Automatic Tristimulus Method; ASTM D5386-16, Standard Test Method for Color of Liquids using Tristimulus Colorimetry; and ASTM D1209-05(2011), Standard Test Method for Color of Clear Liquids (Platinum-Cobalt Scale).

As used herein, "open air count" refers to the transmission value of a haze or color measurement. When measured through an empty chamber, prior to a reference, the open-air count is considered the Reference Open Air Count. When measured during a sample, the open-air count is considered a Sample Open Air Count. As used herein, "open air variation" refers to the acceptable limit of variability of a Sample Open Air Count relative to a Reference Open Air Count.

Apparatus and Components Thereof

Figure 8:
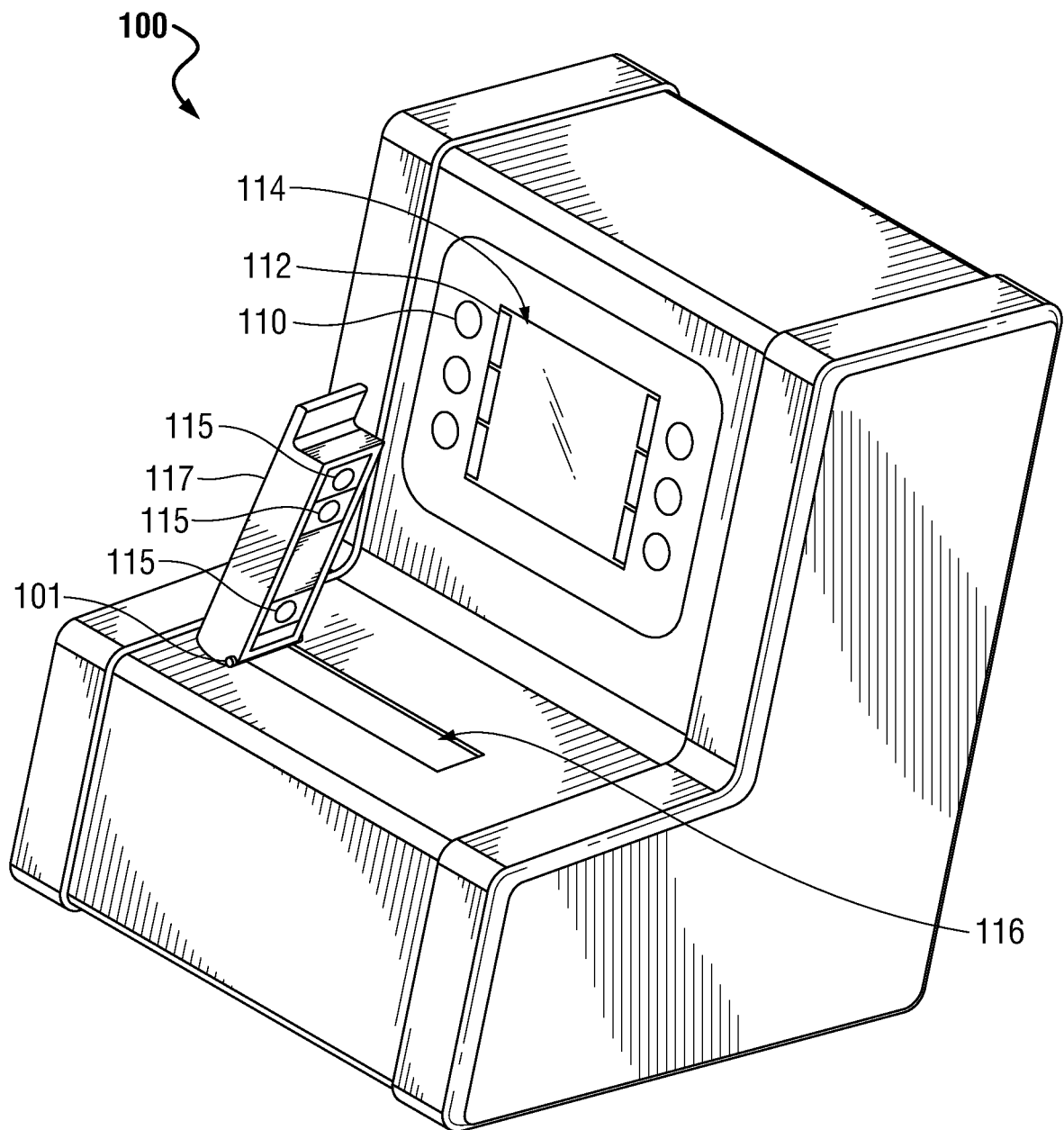
FIG. 8 is a perspective view of the apparatus of FIG. 1 with the sample chamber opened.
Figure 9A:
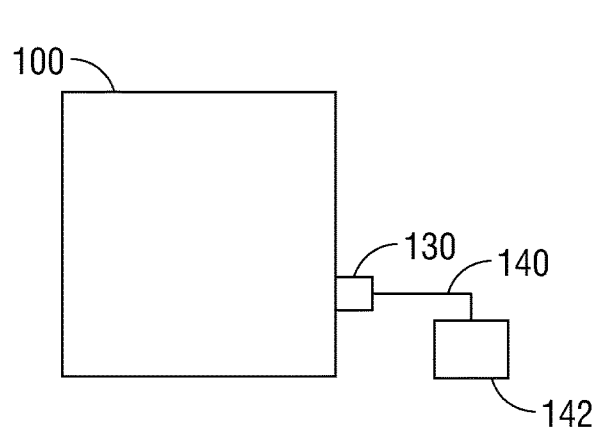
FIGS. 9A and 9B are simplified schematics of the apparatus showing additional features thereof.
Figure 9B:
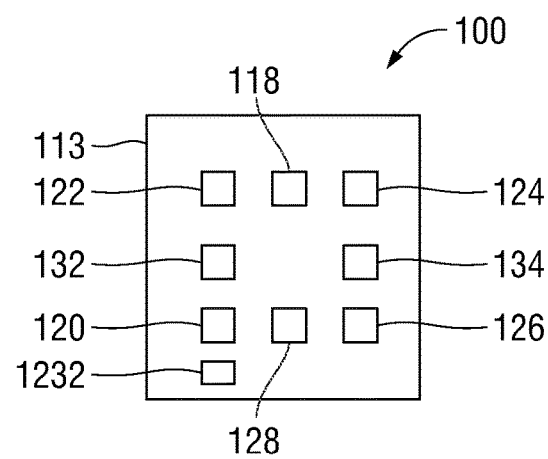

Some aspects of the present disclosure include an apparatus (or system) for analyzing the color, haze, clarity, and/or opacity of liquids, as well as to methods for analyzing the same. FIGS. 1-10 depict an exemplary apparatus in accordance with the present disclosure. Apparatus 100 is a measurement instrument configured to receive liquid samples, and to measure the haze, color, clarity, and/or opacity of the liquid samples. Apparatus 100 includes sample chamber 116 (as shown in FIG. 8) within which liquid samples are placed for optical analysis thereof. Chamber lid 117 may be closed over sample chamber 116 during the optical analysis of liquid samples. In operation, chamber lid 117 can be opened and closed for selective access to chamber 116, such as by pivoting lid 117 about pivot connection 101. As shown in FIG. 8, lid 117 is opened, exposing chamber 116. The lids disclosed herein may include self-alignment features tailored to move or facilitate movement of a cuvette into a proper position within chamber. In FIG. 8, lid 117 includes cuvette clamps 115 as self-alignment features tailored to move or facilitate movement of a cuvette into a proper position within chamber 116. In operation, lid 117 is opened, a sample cuvette is placed into chamber 116, and lid 117 is then closed. Upon closure of lid 117, cuvette clamps 115 are positioned to engage with cuvettes, forcing the cuvettes into position within chamber 116. Cuvette clamps 115 may be or include a ball or protrusion or other member, optionally engaged with a biasing member, such as a spring. Such self-alignment features ensure that sample cuvettes are positioned in the correct position within chamber 116. That is, such self-alignment features ensure that sample cuvettes are positioned along the desired optical pathway within chamber 116 such that color, transmission, and/or scattering measurements of the liquid sample within the sample cuvettes may be measured.

As described in more detail herein, the color, transmission, and scattering through the liquid samples within sample chamber 116 may be measured using apparatus 100. Apparatus 100 includes control buttons 110, which may be programmed to correspond with touchscreen buttons 112 on touchscreen 114 of apparatus 100. Control buttons 110 and/or touchscreen buttons 112 may be used to control the operation of apparatus 100, and touchscreen 114 may present data associated with apparatus 100 and samples being analyzed therein.

Some additional, optional features of apparatus 100 include power switch 120 for turning apparatus 100 on and off, power indicator 118 for indicating when power is on or off, power cord connection 122 for connecting with a power supply, USB connections 124 for transmission of data (e.g., sample analysis data) and/or connection with other apparatus (e.g., keyboards) into or out of apparatus 100, an Ethernet connection 126 for optionally connecting to a network, and a serial port 128 for connection with other apparatus (e.g., external displays). Apparatus 100 may also include air exhausts 132 for exhausting air, as well as air intake 134 for intake of air, which may be at a bottom side 136 of apparatus 100. While data entry into apparatus 100 may be accomplished using touchscreen 114, apparatus 100 may be configured for connection with a printer for printing results and a keyboard or mouse to assist with data entry.

Also, apparatus 100 may include sensor 1232 positioned to sense whether lid 117 is opened or closed.

Apparatus 100 may also include drain port 130 positioned on a side thereof. Drain port 130 may be in fluid communication with sample chamber. In operation, drain hose 140 (e.g., a 2" or 48" hose) may be coupled with drain port 130 and catch or waste container 142 to capture any liquids, such as on the occurrence of a spill within chamber 116.

Touchscreen 114 may present users with one or more menus, each including one or more selectable options for operation of apparatus 100 for testing samples. For example, touchscreen 114 may present one or more menus allowing for selection of tests, including built-in tests; images, including graphs displaying test results; administrative functions, and navigational controls (e.g., to navigate through the various menus and selectable options).

Apparatus 100 may include a computer, including data storage, a processor, and software stored in on a non-transitory storage medium (e.g., the data storage, such as a hard drive or solid-state drive). The software may include computer instructions for instructing the processor to execute various commands and instructions, such as for collecting, computing, and otherwise analyzing the data from spectrometer 400 and photodiodes 306 of apparatus 100.

Housing 113 of apparatus 100 may be resistant to chemical spills and allow for easy clean-up of spills. In some aspects, housing 113 is at least partially or fully composed of a molded plastic of glass filled Nylon. Housing 113 may include feet 1132, which maintain the remainder of apparatus 100 positioned above a surface upon which apparatus 100 resides.

Figure 10:
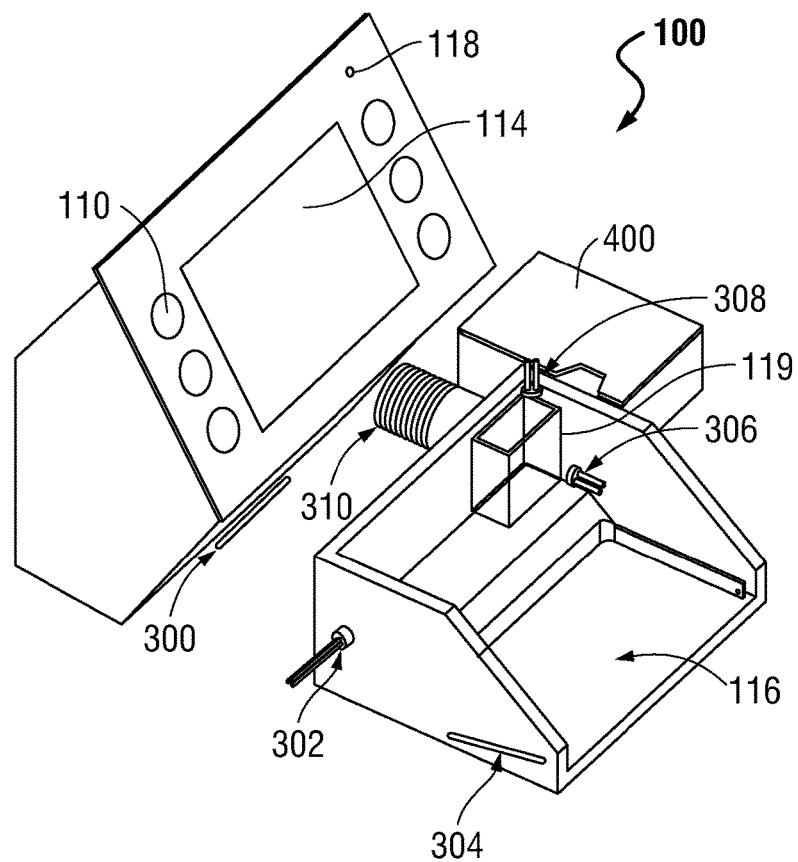
FIG. 10 is an exploded view of portions of the apparatus of FIG. 1.

FIG. 10 is an exploded view of portions of apparatus 100 with lid 117 removed and portions of housing 113 removed, such that the interior of chamber 116 is viewable. Test chamber 116 may accommodate a cuvette (e.g., glass cuvettes) of one or more sizes in a cuvette holder 119 positioned within chamber 116. For example, test chamber 116 may accommodate cuvettes of 10 mm, 33 mm, and/or 100 mm, which, when approximately ⅔ full, may hold about 5 mm, 15 mm, and 45 mm of liquid, respectively.

Test chamber 116 may be coupled with spectrometer 400 for use in attaining spectroscopic measurements of liquid samples within cuvettes. Apparatus 100 may be configured to measure only color, measure only haze, or measure both color and haze. For example, and without limitation, for haze measurements, 15 mm path length cuvettes may be used for transmission and scatter measurements using NIR LED 310 and two photodiodes, one of which is shown as photodiode 306 in FIG. 10. For color measurements, 33 mm and 100 mm path length cuvettes may be used for transmission measurement using white LED 302 and spectrometer 400, which may be a Flame S spectrometer.

For color measurement, light source (white LED 302) and spectrometer 400 specifications may be within the optical range of from 380 nm to 780 nm. In operation, the white light may be diffused through the sample within a cuvette cavity. For haze measurement, light source 310 and photodiode 306 specifications may be within the optical range of from 800 nm to 880 nm. Spectrometer 400 may have a spectral range capable of measuring spectra from ≤350 nm to ≥900 nm, and may have a spectral resolution of ≤3 nanometers. The spectrometer 400 may have a focusing optic for focusing free space light into the slit aperture thereof. In operation, the NIR LED 310 may provide sufficient light directly through the sample into one photodiode 306 and into a second, offset photodiode (not shown)

through back scatter. One skilled in the art would understand that the apparatus and method disclosed herein is not limited to these particular ranges. The operation of any exemplary apparatus is described in more detail below with reference to FIGS. 12-15.

In some aspects, apparatus 100 includes switches or sensors to detect: the size of cuvette inserted into chamber 116, when the lid 117 is open or closed, temperature of haze sample. The cuvettes, when positioned within the test chamber 116, may be positioned within 0.4 mm of the optical reference plane of apparatus 100. The temperature of haze samples may be measured via a non-contact method, prior to and during the sample measurement to within ±2° C. Apparatus 100 includes haze sample thermopile 308 for measuring the temperature of liquid samples before and/or during haze measurements. Apparatus 100 includes internal thermistor 300 and external thermistor 304 for sensing temperature within and external to apparatus 100, respectively.

In some aspects, during use, apparatus 100 is maintained in an environment that is free of direct sunlight, well ventilated, at a temperature ranging from 4 to 38° C., and at a relative humidity (non-condensing) of equal to or less than 85%.

One skilled in the art would understand that the apparatus disclosed herein is not limited to the structure and arrangement shown in FIGS. 1-10.

Color Measurement

To analyze the color of a sample liquid, a user may select the particular color test to perform (e.g., using the touchscreen). For example, the user may select to perform a test in accordance with ASTM D156-15, ASTM D1500-12 (2017), ASTM D6045-12(2017), or ASTM D5386-16.

After selecting the color test, the user may obtain a clean and dry cuvette and then: (1) use a disposable pipette to transfer a small amount of the sample liquid to the cuvette to fill the cuvette approximately halfway; (2) swirl the sample liquid in the cuvette and then dump the sample liquid from the cuvette, ensuring that there is no contamination. After selecting the desired color test, the apparatus may perform an open-air test to determine if the light throughput within the optical path is within acceptable limits. After the open-air test, the user may insert the cuvette containing the sample into the test chamber. The cuvette is seated in cuvette holder, and the test chamber lid is then closed. Upon closure of the test chamber lid, the color test begins automatically. In some aspects, a color measurement test has a duration of two minutes or less. At the conclusion of the test, the apparatus displays the results of the test on the touchscreen. The test results may be printed, saved as a data file (e.g., in text file format), or combinations thereof.

References is herein made to Appendix A of incorporated U.S. Provisional Patent Application No. 62/689,726 (the '726 Application), which details the use of one exemplary apparatus in accordance with the present discourse for the purposes of implementing a color test, and is incorporated herein by reference in its entirety. Thus, one skilled in the art would understand that incorporated Appendix A may be referenced in implementing a color test in accordance with certain aspects of the present disclosure. However, one skilled in the art would also understand that the present disclosure is not limited to the particular exemplary apparatus and method shown and described in incorporated Appendix A.

Haze/Clarity/Opacity Measurement

Some aspects of the present disclosure include an apparatus (or system) for analyzing the haze, clarity, and/or opacity of liquids, as well as to methods for analyzing the haze, clarity, and/or opacity of liquids. The apparatus may be the same apparatus as described herein for use in color measurement. Thus, in some aspects the apparatus is capable of both haze, clarity, opacity, and color measurement and/or analysis.

With a cuvette of a sample liquid within test chamber 116, testing may be performed. The haze, clarity, and opacity testing may include performing: (1) a single test of the sample liquid, (2) multiple tests of the sample liquid, (3) timed tests of the sample liquid, or (4) a haze-at-temperature test of the sample liquid. The single and multiple tests may be executed for pre-defined lengths of time, as described in more detail elsewhere herein. The sample preparation may follow the same or substantially the same process for each of the four haze, clarity, opacity test options. To perform a test, a cuvette of a sample liquid may be shaken for a period of time. The cuvette may then be inserted into the test chamber 116 in the cuvette holder, the lid 117 may be closed, and the test may then be initiated, beginning with an open-air test and followed by the sample test. In some aspects, a haze measurement test has a duration of two minutes or less. In certain aspects, apparatus 100 may take continuous haze measurements of a single sample for up to sixty minutes. After the test is completed, touchscreen 114 may display the test results, which may be printed, saved as a data file, or combinations thereof.

Figure 11A:
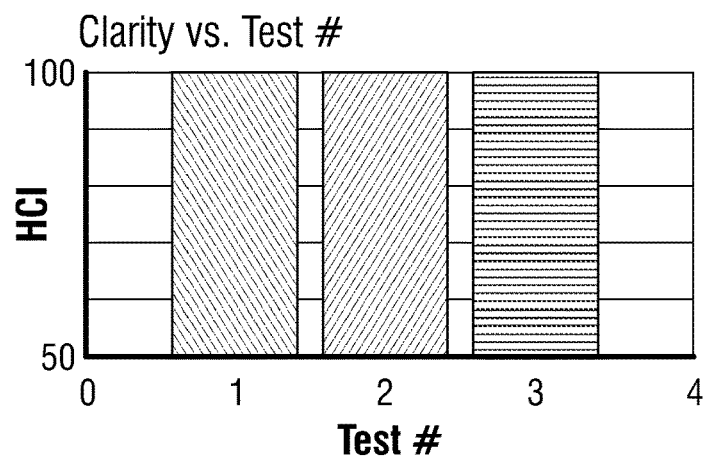
FIG. 11A is a bar graph of HCI vs. test performed.
Figure 11B:
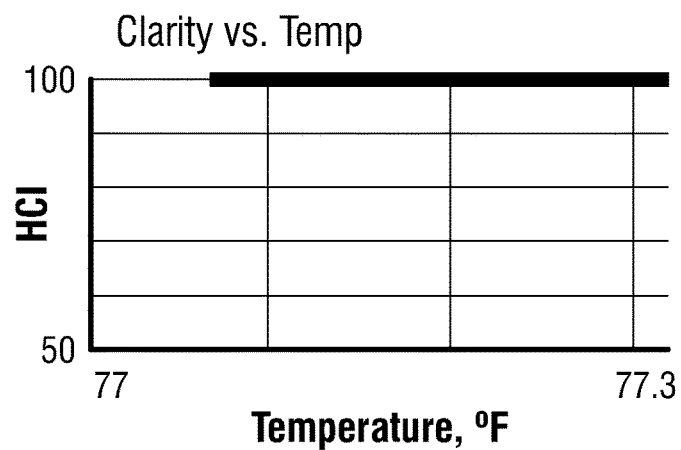
FIG. 11B is a graph of HCI vs. temperature of sample.
Figure 11C:
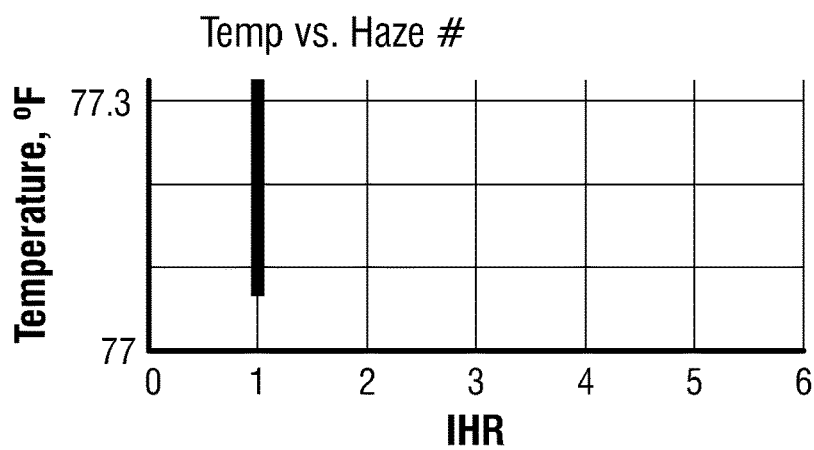
FIG. 11C is a graph of temperature of sample vs. IHR.

The results of the haze, clarity, and opacity test may be in the form of: a graph of clarity (HCI) vs. test number, an example of which is shown in FIG. 11A; a graph of clarity (HCI) vs. temperature, an example of which is shown in FIG. 11B; a graph of temperature vs. haze number (IHR), an example of which is shown in FIG. 11C; or combinations thereof.

For timed tests, the total testing duration may be selected. For example, testing may be set to run for two minutes. The number of tests performed over the total testing duration will depend on the selected individual test duration, which may also be set. For example, if the total testing duration is set at two minutes, and the individual testing duration is set at 10 seconds with 0 seconds between each individual test, then twelve tests will be performed over the two minutes (i.e., 120 seconds±10 second per test=12 tests).

The haze at temperature test provides the ability to set a desired temperature for the measurement, and to manipulate the temperature of the sample liquid to achieve a measurement at the temperature of interest. For example, a test may be set to capture data at 67 degrees Fahrenheit. Thus, prior to mixing a sample liquid, the sample may be brought to temperature, allowing the temperature of interest to be attained in the sample. If the temperature of interest is below the ambient temperature, then the cuvette and sample are cooled to below the set point of interest and allowed to heat up to the temperature of interest within the sample chamber. Apparatus 100 may be set (e.g., programmed) to measure the color and/or haze of the sample and collect data only when the sample is within the temperature region of interest. For example, the temperature region of interest may be defined as a set temperature ±1 degree Celsius. If the temperature setting is above the ambient temperature of the system, then the cuvette and sample may be heated beyond the temperature of interest and allowed to cool to the set point within the sample chamber. Temperature of the sample may be measured using thermocouple 308. Once the desired sample temperature is attained, the data (e.g., a graph) may appear on touchscreen displaying the sample temperature and horizontal lines to demonstrate the temperature region of interest for the measurement. As more measurements are taken, the graph may be populated with the temperature curve of the sample as it approaches and passes through the temperature region of interest. If multiple data points are collected through the temperature region of interest, the results may be averaged together and presented in graphs showing test results. If only a single data point is collected through the temperature region of interest, the results will show a single measurement.

References is herein made to Appendix B of incorporated the '726 Application, which details the use of one exemplary apparatus in accordance with the present discourse for the purposes of implementing a haze/clarity/opacity test, and is incorporated herein by reference in its entirety. Thus, one skilled in the art would understand that incorporated Appendix B may be referenced in implementing a haze/clarity/opacity test in accordance with certain aspects of the present disclosure. However, one skilled in the art would also understand that the present disclosure is not limited to the particular exemplary apparatus and method shown and described in incorporated Appendix B.

Administration of Apparatus

Apparatus 100 may be a fully-integrated, standalone system capable of quickly and accurately measuring the color, haze, clarity, and/or opacity of liquids, such as petroleum products, and providing and presenting the measurement results in an easy to understand format. For example, in some aspects, apparatus 100 is a touch-screen and menu driven system, allowing users to quickly and easily obtain accurate color measurement results.

Apparatus 100 may be configured to transfer data from apparatus 100 to other devices and storage medium, such as via a wireless network or wired connection, for example using USB ports 124 or ethernet port 126. One skilled in the art would understand that apparatus 100 is not limited to these particular communication ports. Apparatus 100 may also be configured for the copying, deleting, and searching of data files, including saved teste measurement data files.

In some aspects, apparatus 100 allows testing settings to be selected and/or modified and/or adjusted. For example, the sample shaking (or swirling) time, time allowed to transfer the sample to the cuvette, time between scans when performing multiple scans, haze reference limits, color coefficients, temperate settings, intensity of the near infrared (NIR) light emitting diode (LED), spectroscopic parameters, and open-air variation value may be selected and/or modified and/or adjusted using apparatus 100. In some aspects, the sample shaking time is at least 20 seconds. The time between scans may range, for example, from 400 to 300,000 ms between each scan. Apparatus 100 may also provide for the calibration of each test apparatus 100 is capable of performing.

References is herein made to Appendix C of incorporated the '726 Application, which details the use of one exemplary apparatus in accordance with the present discourse for the purposes of administration of the apparatus, and is incorporated herein by reference in its entirety. Thus, one skilled in the art would understand that incorporated Appendix C may be referenced in implementing administration of the apparatus in accordance with certain aspects of the present disclosure. However, one skilled in the art would also understand that the present disclosure is not limited to the particular exemplary apparatus and method shown and described in incorporated Appendix C.

Operation of an Exemplary Apparatus

With reference to FIGS. 12-15, operation of an exemplary apparatus will now be described.

Figure 12:
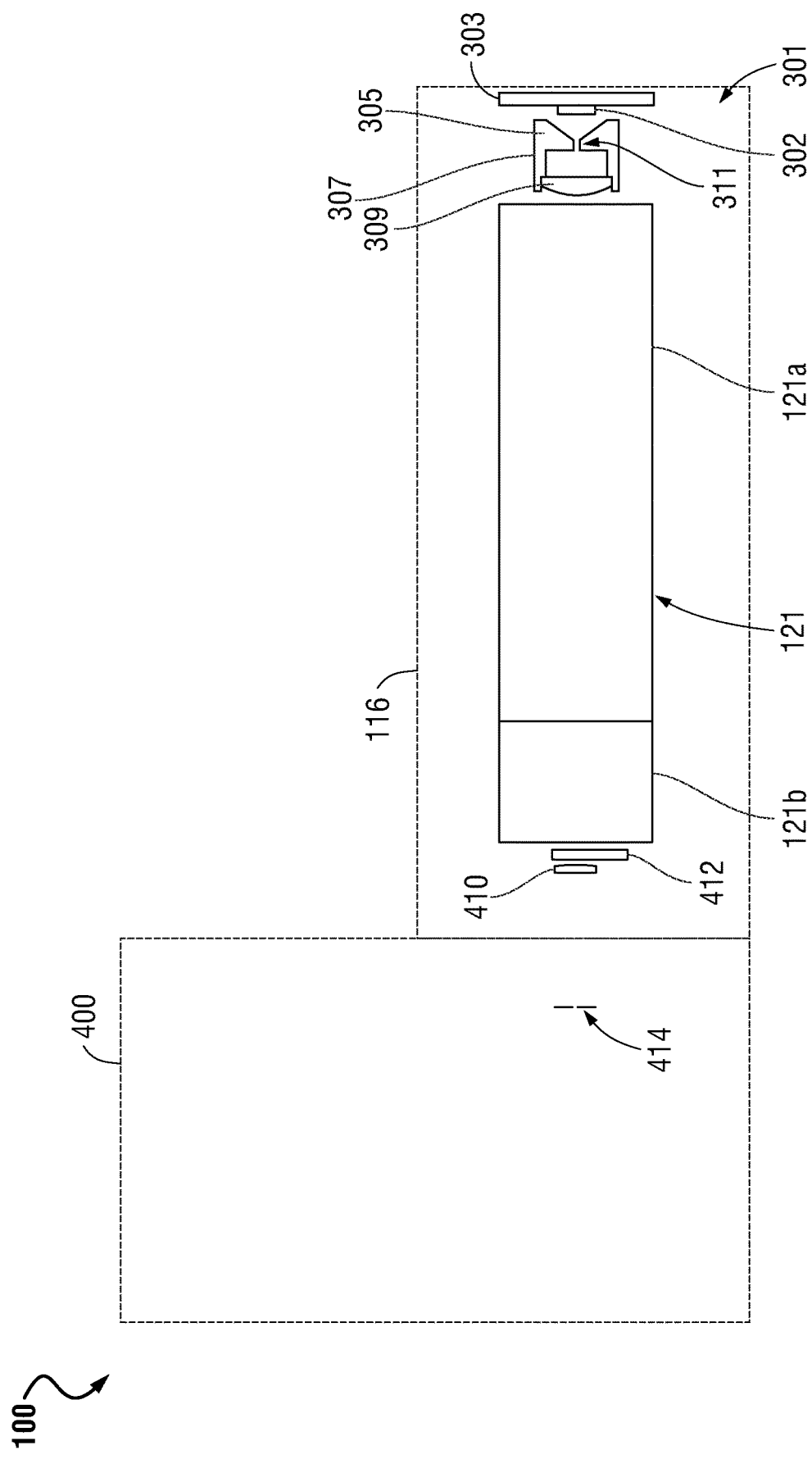
FIG. 12 is a simplified schematic of an exemplary analyzer or measurement instrument, according to the present disclosure, showing features associated with color measurement.

FIG. 12 is a simplified schematic of apparatus 100 capable of performing color, haze, and clarity measurements in sample of liquid, such as fuel or lubricant. Apparatus 100 is a single instrument having a unitary housing (e.g., housing 113) supporting the measuring instrumentation for measuring each of color, haze, and clarity.

Apparatus 100 includes spectrometer 400 that is optically coupled with chamber 116, such that chamber 116 and spectrometer 400 are positioned in functional relation to and adjacent one another.

Chamber 116 includes sample cuvette 121, which includes large cuvette 121a and small cuvette 121b. In one aspect, apparatus 100 and, more specifically, chamber 116 accommodates cuvettes of variable lengths and provides for measurement of samples in cuvettes of variable lengths.

Apparatus 100 includes light source 301 for providing light to be transmitted through a sample liquid and, ultimately, into spectrometer 400 for analysis therein. As shown in FIG. 12, light source 301 is a white light illuminator including a white LED 302 coupled with a white LED circuit card assembly 303, flux collector 305, cylindrical diffuser 307, and illuminating formatting optics (lens) 309.

Collection lens 410 is disposed within chamber 116 such that electro-magnetic radiation (light) passing into spectrometer 400 for analysis therein first passes through collection lens 410. Also, chamber window 412 is positioned within chamber 116 to facilitate optical communication between sample cuvette 121 and spectrometer 400. Light passing out of sample cuvette 121 first passes through chamber window 412, then through collection lens 410, and then through spectrometer input slit 414 to enter into spectrometer 400 for analysis therein.

Figure 13:
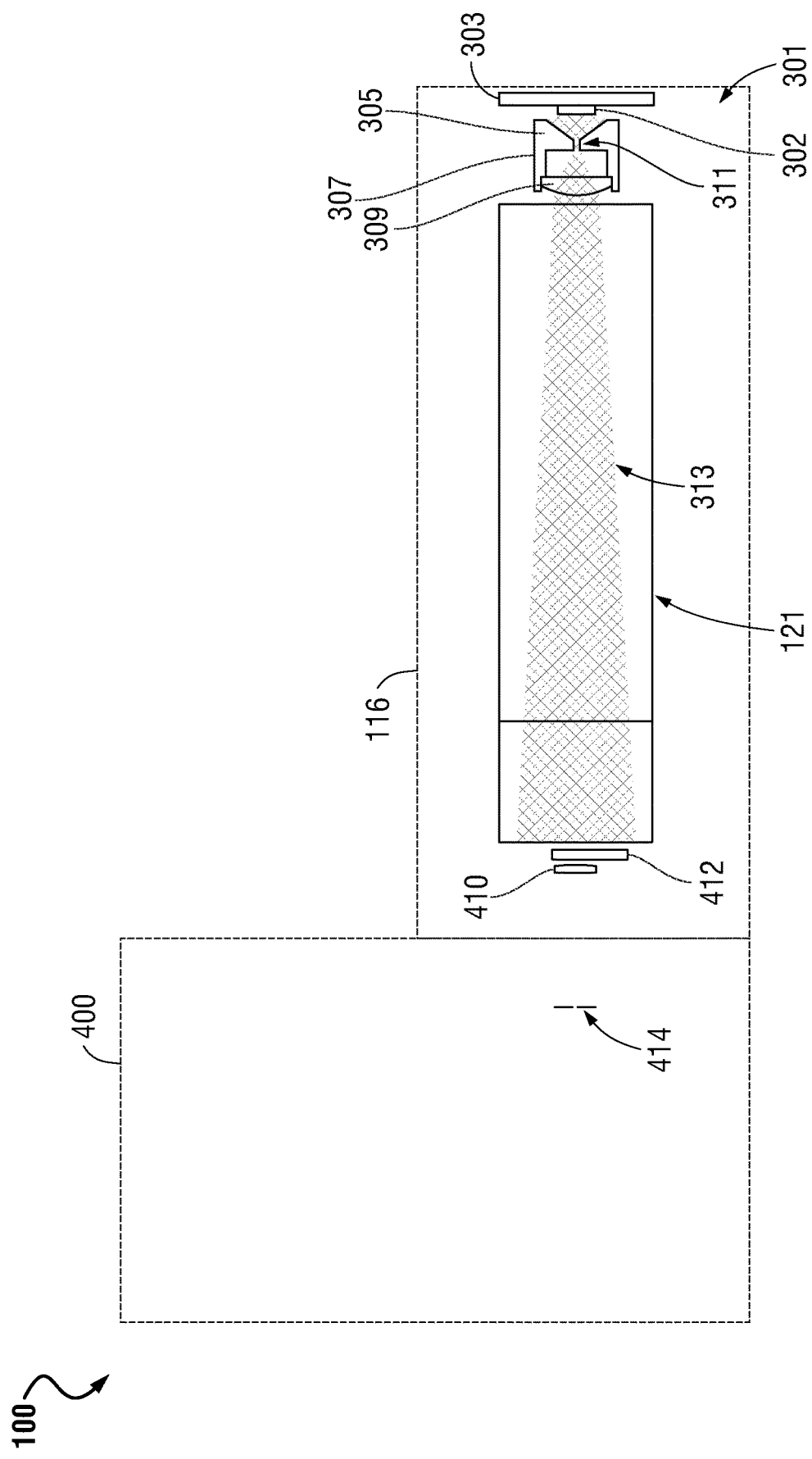
FIG. 13 is a simplified schematic of the apparatus of FIG. 12 showing an illuminator path within a sample chamber.

With reference to FIG. 13, the illuminator path of beam 313 within apparatus 100 for the components shown and described with reference to FIG. 12 is depicted. In operation, white LED 302 transmits white light, which is collected by flux collector 305, which tapers to an aperture 311 smaller than the beam of light emitted from the light source 302. The light beam 313 is concentrated by the small aperture 311, and then passes into cylindrical section 307, which has a diameter larger than that of small aperture 311, such that the beam 313 diffuses and passes, creating an extended depth source of light. Cylindrical diffuser 307 provides the white light beam 313 to illumination formatting optics 309. In operation, illumination formatting optic 309 collimates or nearly collimates beam 313 for introduction into cuvette 121. Depending on the particular application, apparatus 100 may include illumination formatting optic(s) 309 that provide various different degrees of collimation. The degree of collimation correlates to divergence of illumination beam 313. In some aspects, various degrees of divergent illumination may be used. The amount of divergence of the light may vary with, for example, the application at hand or the state of an evolving liquid being analyzed. White light beam 313 then passes into sample cuvette 121, through any sample liquid contained within sample cuvette 121, through chamber window 412, through collection lens 410, and through input slit 414 for analysis within spectrometer 400. Within spectrometer 400, the light may be analyzed by methods well known to those skilled in the art to determine optical data regarding the color of the sample liquid. As discussed previously, this optical data may be presented in various forms. The pathway of light from light source 302 into spectrometer 400 defines an optical pathway or color detection channel.

While shown and described as using a white light, the present disclosure is not limited to use of only white light, and may include use of a light source with a more narrow or broad range of wavelengths, including visible light.

Figure 14:
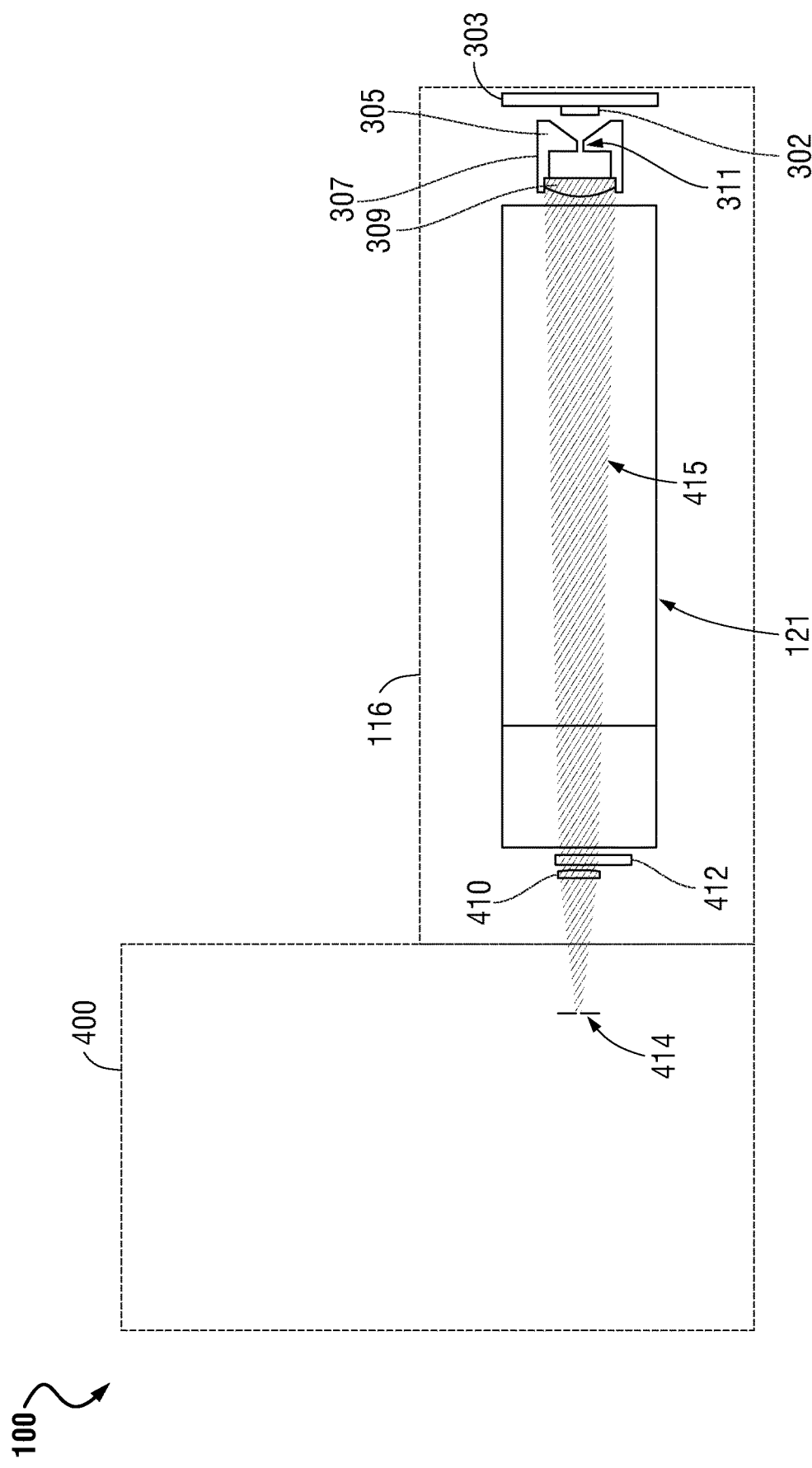
FIG. 14 is a simplified schematic of the apparatus of FIG. 12 showing collection path to a spectrometer.

With reference to FIG. 14, the collection path 415 of spectrometer 400 is depicted. As shown, collection lens 410 gathers light from an area that is as large or larger than the illuminator aperture, which is then transmitted through input slit 414 into spectrometer 400. The collection angle may be chosen to accommodate anisotropic effects in sample liquids, such as thermal gradients, varying densities, or varying viscosities.

With reference to FIG. 15, apparatus 100, which may be the same apparatus as shown and described above with reference to FIGS. 12-14, is depicted highlighting the portions of apparatus 100 that provide for haze and clarity measurements. Apparatus 100 in FIG. 15 may also include all of the components of apparatus 100 of FIGS. 12-14, some of which are not shown in FIG. 15 for clarity. Apparatus 100 includes light source 310, which may provide light of a small wavelength band or broadband. For example, light source 310 may be an NIR LED light. Apparatus 100 may be equipped with non-spherical refractive surfaces 422 to control divergence from light source 310. In some aspects, spherical optics may also be used to control divergence from light source 310.

Apparatus 100 may include two detection channels. A first detection channel may be used to measure loss of light through sample liquid contained within the small cuvette 121b, and a second detection channel may be used to measure scatter of light through sample liquid contained within the small cuvette 121b. Along the first detection channel, light may pass from light source 310, through divergence control optics 422, through chamber window 413a, and through sample liquid contained within the small cuvette 121b. Light that is not lost in passing through the sample liquid passes through chamber window 413b and to photodetector 306a for detection thereby. Along the second detection channel, light may pass from light source 310, through divergence control optics 422, and through chamber window 413a into the sample liquid contained within the small cuvette 121b. At least some of the scattered light within the sample liquid may pass through chamber window 413c and to photodetector 306b for detection thereby. The photodetectors 306a and 306b may be in data communication with a computer of apparatus 100, which may receive data signals from photodetectors 306a and 306b that correlate to the light detected by photodetectors 306a and 306b. These data signals may then be processed (e.g., via use of computer instructions) to determine data about the haze and clarity of the sample liquid. This data, as discussed elsewhere herein, may be presented in any of numerous formats, including graphically on touchscreen 114.

Thus, apparatus 100 includes two detection channels used to: measure the loss of light through the sample; and measure the scatter of light through the sample via interaction with water or solid particles in the sample liquid. The light transmission detector (photodetector 306a) may include tandem apertures 420 to limit the volume of sample used in measurements. A nephelometer (photodetector 306b) may be used to measure the scatter of light through the sample. The nephelometer channel (second channel) may include lens 417 to collect consistent scatter volume in the channel.

Sample Analyzer Capable of Measuring Color, Haze, and Clarity

Certain embodiments of the present disclosure include an apparatus capable of measuring the color, haze, and/or clarity of a liquid sample, within a single device, as well as to methods making and using the same. In some such aspects, the color, haze, and/or clarity of a liquid sample may be measured within the same test chamber of the same apparatus.

FIGS. 1-10 and FIGS. 12-15 depict an apparatus in accordance with the present disclosure that is capable of measuring the color, haze, and clarity of a liquid sample. To achieve the ability to measure each of color, haze, and clarity of a liquid sample, apparatus 100 includes sample cuvette 121, which includes two chambers, defining a large cuvette 121a (e.g., for color measurements) and a small cuvette 121b (e.g., for haze/clarity measurements). Additionally, apparatus includes a spectrometer 400 in optical communication with the sample chamber 116, a white LED light 302 in optical communication with the sample chamber 116, and an NIR LED source 310 in optical communication with the chamber 116, and photodetectors 306, each positioned, relative to the liquid sample and the chamber 116 to measure at least one particular optical characteristic of the liquid sample within chamber 116, as described herein.

Apparatus 100 combines techniques of measuring both transmission and scatter, such that each measurement technique (transmission or scatter) provides a check against the other measurement technique. A computer of apparatus 100 may include computer instructions for executing an algorithm that combines the measurements (transmission and scatter) into two scales. One such scale corresponds to the haze rating scale of from 1 to 6 of the ASTM D4176 procedure B, which is used in the petroleum industry for the rating a fuels relative haziness or cloudiness. The algorithm also produces a result referred to as the Haze Clarity Index (HCI), which is a component of the ASTM STM D8148-17 procedure. By using the (HCI) values, rather than the haze rating scale of from 1 to 6 of the ASTM D4176 procedure B, apparatus 100 provides a user (e.g., producer or transporter) with greater specificity and tighter control parameters in comparison to that provided by the haze rating scale of from 1 to 6 of the ASTM D4176 procedure B.

Sample Analyzer with Timed or Prompted Sample Testing

Certain aspects of the present disclosure include an apparatus capable of timed sample testing; capable of prompted, multiple sample tests; or combinations thereof to yield data representing the optical characteristics of a sample (e.g., a fuel sample), as the sample settles from an agitated state to a settled, non-agitated state. Thus, a sample of liquid, in an agitated state, may be inserted into the chamber 116 of apparatus 100, and apparatus 100 may be programmed (e.g., via computer instructions) to measure the color, haze, and/or clarity of the sample over a certain period of time and at certain increments of time, while the sample of liquid settles from the agitated state to a settled, non-agitated state. For example, and without limitation, apparatus 100 may be programmed to measure the color, haze, and/or clarity of the sample over a period of sixty minutes, with repeated, individual measurements of the sample taken every twelve seconds. As such, the color, haze, and/or clarity of the sample may be determined with the sample at various states of agitation. The test results may be in the form of data graphs, including plots of clarity vs. individual test performed, clarity vs. time at which the individual test was performed, clarity vs. temperature of the sample when the individual test was performed, temperature of the sample vs. haze, or combinations thereof. The test results are not limited to being presented in these particular, exemplary formats.

In some aspects, rather than apparatus 100 being programmed to automatically perform such timed tests at programmed intervals for a programmed duration, apparatus 100 may be programmed to prompt a user to perform such tests at certain intervals for a certain duration. For example, apparatus 100 may present such prompts to users on touchscreen 114.

Sample Analyzer with Self-Alignment Features

Figure 16C:
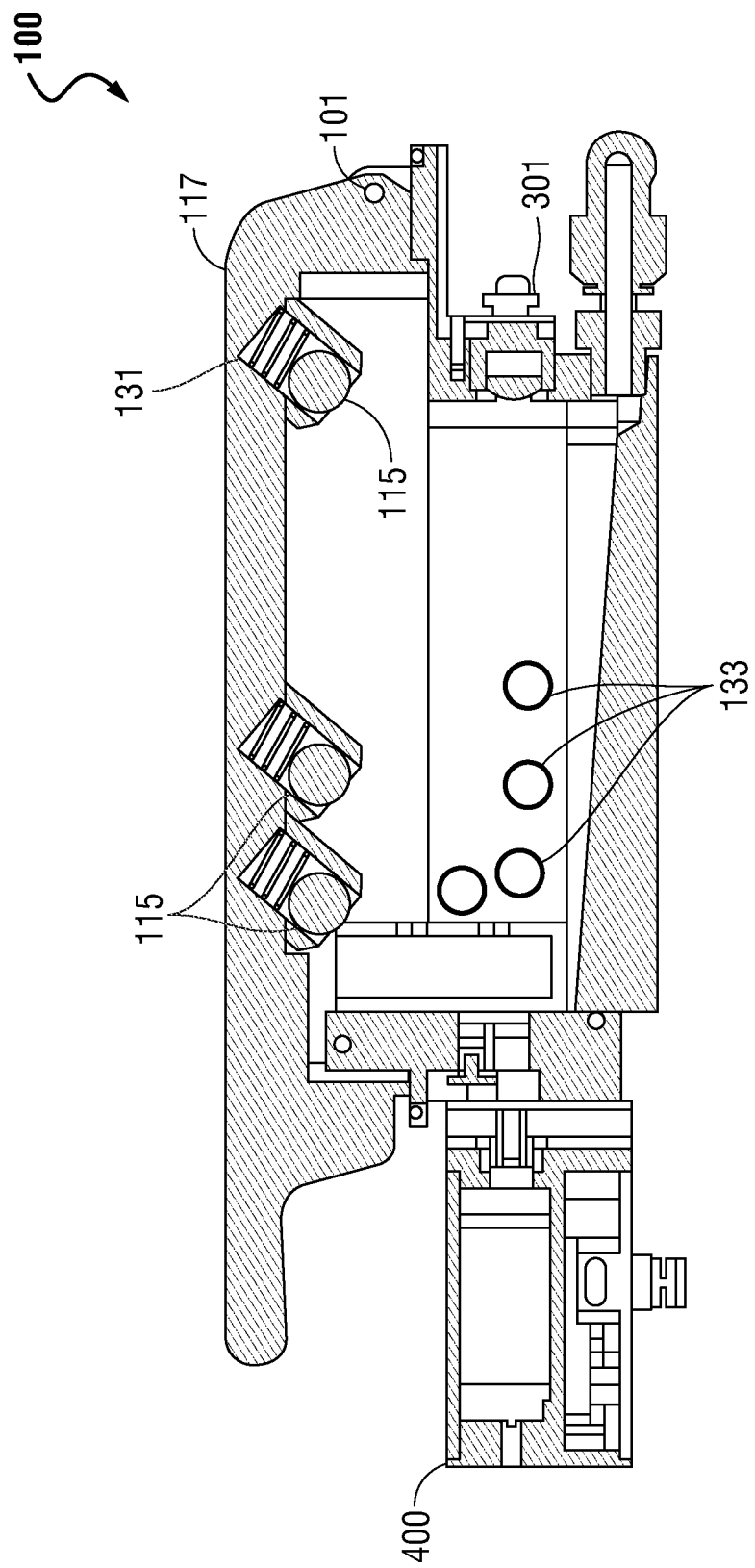
FIG. 16C is a cross-sectional view the instrument of FIG. 16A, without a cuvette installed in the chamber.

Certain aspects of the present disclosure include an apparatus including one or more self-alignment features (e.g., force applicators) tailored to move or facilitate movement of a sample cuvette into a proper position within chamber 116 for analysis thereof when lid 117 is closed. As discussed above, FIG. 8 depicts one exemplary self-alignment feature tailored to move or facilitate movement of a cuvette into a proper position within chamber 116, including cuvette clamps 115. With reference to FIGS. 16A-16C, clamps 115 may include a ball or other member engaged with biasing member, such as spring 131. Apparatus 100 may include sensors 133 positioned to detect the presence, size, and/or position of cuvettes installed within the chamber 116. Cuvette 121 is shown engaged with the leftmost clamp 115 in FIG. 16B, with the leftmost sensor 133 in FIG. 16B, closest to cuvette 121, positioned to detect the presence of cuvette 121.

Sample Analyzer with Sensors to Confirm Cuvette Size

Certain aspects of the present disclosure include an apparatus including sensors 133 positioned within chamber 116 and capable of determining if a proper-sized cuvette has been installed within the chamber for the test measurement being performed. For example, the sensors 133 may include plunger sensors or proximity sensors. Each sensor 133 may be in data communication with a computer of apparatus 100 to transmit data signals thereto that are representative of: whether a cuvette has been placed into the chamber 116; and, if a cuvette has been placed into the chamber 116, whether the cuvette is the proper sized cuvette. Whether or not the cuvette is the proper sized cuvette may depend on, for example, the particular measurement test being conducted (e.g., color or haze). The sensors 133 may detect the dimensions, weight, and/or presence of cuvettes, depending on the particular sensor used. In operation, a data signal from the sensor 133 (or the absence thereof) may initiate generation of a prompt by apparatus 100 (e.g., via computer instructions) to a user that a cuvette has been placed into the chamber 116, a cuvette has not been placed into the chamber 116, the cuvette in the chamber 116 is the proper sized cuvette, or the cuvette in the chamber 116 is not the proper sized cuvette. The prompt may be an audible prompt (e.g., a beep from a speaker), a visible prompt (e.g., a message on touchscreen 114), or combinations thereof. For example, as shown in FIG. 16B, apparatus 100 includes three sensors 133. The view of the leftmost sensor 133, positioned on the left side of chamber 116 in FIG. 16B, is partially obstructed by the presence of sample cuvette 121 positioned adjacent the left-most sensor 133. Thus, as shown, apparatus 100 detects that sample cuvette 121 is of a size sufficient to trigger the left-most sensor 133, but not the middle and right-most sensors 133. Thus, the left-most sensor 133 indicates that a cuvette has been positioned within the chamber 116, and the fact that only the left-most sensor 133 is triggered is indicative of the size of the cuvette within the chamber 116.

Figure 17:
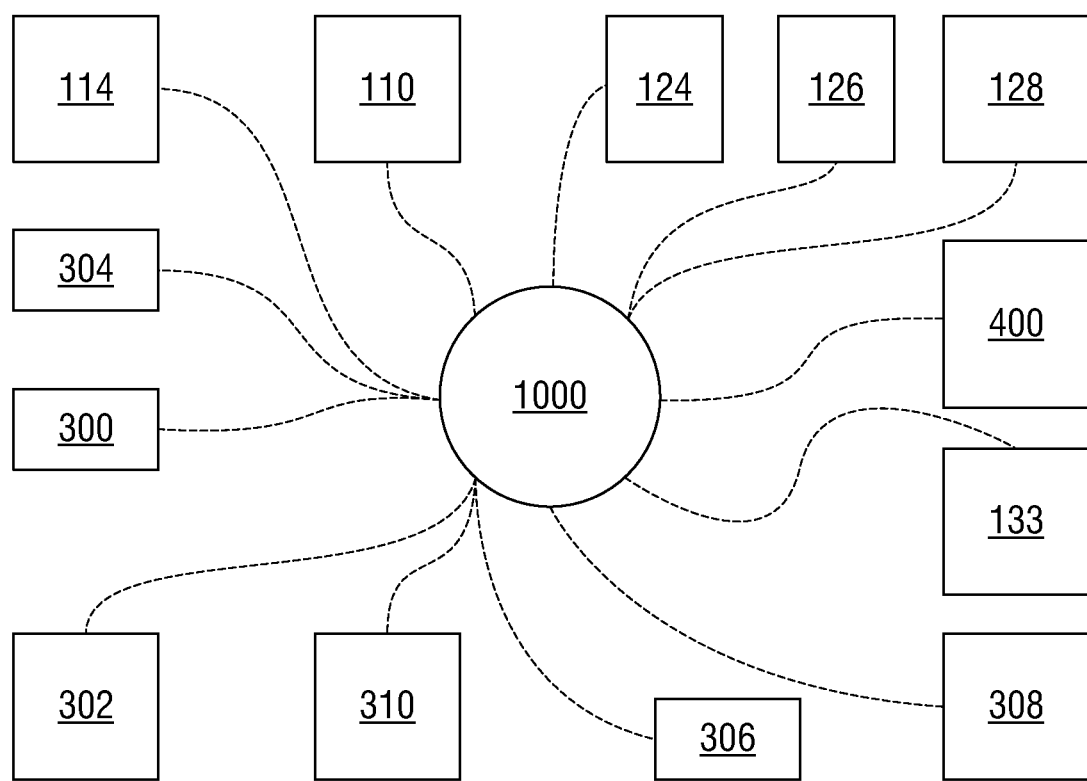
FIG. 17 is a simplified schematic showing data and/or electronic coupling between various components of an exemplary analyzer or measurement instrument, according to the present disclosure.

FIG. 17 depicts a schematic of the data communication between computer 1000 of the apparatus disclosed herein and various other components of the apparatus. Computer 1000 may be in data and/or electronic communication with display 114 for receiving and responding to commands therefrom, such as via a user pressing a touchscreen button, and for presenting data on the touchscreen 114, such as test results. Computer 1000 may be in data and/or electronic communication with buttons 110 for receiving and responding to commands therefrom, such as via a user pressing the buttons 110. Computer 1000 may be in data communication with outputs and/or inputs, such as USB 124, ethernet 126 and serial 128, for receiving and/or transmitting data or commands. Computer 1000 may be in data and/or electronic communication with spectrometer 400 for receiving data therefrom, and for sending control commands thereto. Computer 1000 may be in data and/or electronic communication with plunger or proximity sensors 133, photodiodes 306, thermocouple 308, and thermistors 300 and 304 for receiving sensor data therefrom. Computer 1000 may be in data and/or electronic communication with light sources 310 and 302 for sending control commands thereto.

As would be understood by one skilled in the art, computer 1000 may include data storage (e.g., non-transitory data storage) and a processor for executing computer instructions for the control of components, the collection of data from components, and the analysis of data. As such, computer 1000 may be used to configure and control, via computer instructions, each component of the apparatus, including those not specifically shown in FIG. 17. In some aspects, computer 1000 is a programmed logic controller (PLC).

Applications

The apparatus and methods disclosed herein may be used by fuel producers, users and transporters to determine color, haze, clarity and quality of fuels. While described as applicable to fuels, lubricants, and other petroleum-based products, the apparatus and methods disclosed herein are not limited to these liquids, and may be applied to products other than petroleum-based products, fuels, and/or lubricants.

EXAMPLES

Testing Procedures

The following are examples of implementations of testing procedures using the apparatus disclosed herein. One skilled in the art would understand that the present disclosure is not limited to performance of these particular steps in the particular orders discussed.

Example 1

Color Measurement Test Procedure

To analyze the color of a sample liquid, a user may select the particular color test to perform (e.g., using the touchscreen). For example, the user may select to perform a test in accordance with ASTM D156-15, ASTM D1500-12 (2017), ASTM D6045-12(2017), or ASTM D5386-16.

After selecting the color test, the user may obtain a clean and dry cuvette and then: (1) use a disposable pipette to transfer a small amount of the sample liquid to the cuvette to fill the cuvette approximately halfway; (2) swirl the sample liquid in the cuvette and then dump the sample liquid from the cuvette, ensuring that there is no contamination.

After selecting the desired color test, the apparatus may perform an open-air test. After the open-air test, the user may insert the cuvette containing the sample into the test chamber. The cuvette is seated in cuvette holder, and the test chamber lid is then closed. Upon closure of the test chamber lid, the color test begins automatically. At the conclusion of the test, the apparatus displays the results of the test on the touchscreen. The test results may be printed, saved as a data file, or combinations thereof.

Saybolt Test—If the Saybolt test, in accordance with ASTM D156-15, is selected as the color test, a 100 mm cuvette may be used for sample analysis. The reference material for a Saybolt test may be dodecane. The Saybolt test begins with an Open Air Test. After the Open-Air Test is completed, the cuvette containing the sample liquid is inserted into the testing chamber for testing, against a cuvette holder, and the chamber lid is firmly closed. Upon completion of the test, the test results are displayed on the touchscreen.

ASTM Test—If the ASTM test, in accordance with ASTM D1500-12(2017), is selected, a 33 mm cuvette may be used for the sample analysis, and may follow the same or substantially the same steps as described above in reference to the Saybolt Test.

Platinum Cobalt Test—If the platinum Cobalt test, in accordance with ASTM D1209-05(2011), is selected, a 100 mm cuvette for sample analysis may be used, and may follow the same or substantially the same steps as described above in reference to the Saybolt Test. The reference material for the Platinum Cobalt test may be distilled water.

Example 2

Color Reference Test Procedure

Reference test procedures may be performed on a periodic basis, including when a significant change in the test environment (e.g., change in temperature) has occurred. The process for a Reference Test is identical for the ASTM, Saybolt and Platinum Cobalt tests, with the exception of the cuvette size and the standards used. For example, the ASTM reference test steps may include: (1) clean all optical windows in the teste chamber by spraying a lint free wipe with isopropyl alcohol and drying with an optical swab; (2) select "Reference" from the Select Sample Test Name screen; (3) when prompted, insert a clean and dry cuvette of the specified size; and (4) run the test.

Example 3

Haze/Clarity/Opacity Measurement Test Procedure

To perform a haze, clarity, and opacity test, a user may select the haze test on the touchscreen, and then select to perform a single test, multiple tests, a timed test, or a haze-at-temperature test. The single and multiple tests may be executed for a pre-defined length of time. The sample preparation may be the same each test.

The user may first obtain a clean and dry cuvette, and perform the following steps: (1) shake a container of the liquid sample for 15 seconds; (2) verify that there is no sediment on the bottom of the container; (3) use a disposable pipette to transfer a small amount of the sample liquid to the cuvette to fill approximately halfway; and (4) swirl the liquid in the cuvette and then dump the liquid to dispose of the rinse liquid. These steps may ensure that there is no contamination in the test.

The user may then verify that there is not a cuvette in the test chamber of the apparatus, and then initiate an open-air test. Once the open-air test is complete, the user may shake the sample liquid for a period of time, use a pipette to fill the cuvette with 5 ml of sample solution such that the cuvette is approximately ⅔ full, wipe any liquid or smudges from the outside of the cuvette with a lint free wipe, insert the cuvette into the chamber in a cuvette holder, close the chamber lid, and begin the sample test. When the test is complete, test results will be displayed on the touchscreen, which may be saved, printed, or both.

Example 4

Haze/Clarity/Opacity Reference Test Procedure

A Reference Test may be, at times, performed, following a procedure that the same or substantially the same as the sample test procedure described in Example 3. The Reference Sample may be dodecane.

Exemplary calibrations of for haze and color measurements are provided in more detail within incorporated Appendices A, B, and C.

Example 5

Spectroscopic Determination of Haze in Fuels

As described elsewhere herein, the IHR and HCI may be determined in accordance with the test procedures of ASTM D8148-17, the entirety of which is incorporated herein by reference.

Scope—This test method covers a spectroscopic procedure for determining the level of suspended water and particulate contamination (haze) in liquid middle distillate fuels, including those blended with synthesized hydrocarbons or biofuels. An ordinal, whole-number, Instrument Haze Rating (IHR) from 1 to 6 and a Haze Clarity Index (HCI) from 50.0 to 100.0 are determined on a test specimen at a temperature of $22.0°$ C.$±2.0°$ C.

The HCI is a numerical value of from 50.0 to 100.0 that indicates fuel clarity, as derived from spectroscopic measurements, as processed via an algorithm. The IHR is an ordinal, whole number of from 1 to 6 that corresponds to haze ratings as defined in ASTM D4176, Procedure 2, and is assigned to a specimen based on spectroscopic measurements, as process by an algorithm. Specimens are considered optically clear when the specimen is transparent to light having wavelengths ranging from 340 to 2500 nm.

Summary of Test Method—The test unit (sample) is conditioned (allowed to heat or cool) to a test temperature of $22.0°$ C.$±2.0°$ C. Optics, software, and calibration materials are used to provide a numerical Instrument Haze Rating (IHR) and Haze Clarity Index (HCI) of the fuel sample after a test specimen is placed into an optically clear cuvette and measured according to Beer-Lambert Law for percent transmittance and nephelometric principles for percent light scatter. These IHR and HCI are obtained by comparison of the measurements to a previously prepared calibration curve and applied to an algorithm to obtain: (1) the IHR of from 1 to 6; and (2) the HCI of from 50.0 to 100.0, which may be used to evaluate haze intensity in general.

Apparatus—The apparatus used in the testing, and the apparatus disclosed elsewhere herein, may meet one or more of the following specifications: (1) the apparatus is portable and a self-contained unit operating on an alternating current (ac) power source (power cords may be furnished for various voltages); (2) the spectrometer, nephelometric sensors, and test specimen temperature measuring devices of the apparatus are positioned in the test specimen cuvette chamber of the apparatus; (3) the spectrometer/nephelometer includes or consists of a combination of a near-infrared (NIR) light-emitting diode (LED) light source and photodiodes positioned to measure transmission and scatter across the test specimen; (4) the temperature measuring device of the apparatus is a non-contact infrared (IR) thermopile-based temperature sensor, with an accuracy of 62.0° C. and a range of 4.0° C. to 38.0° C.; (5) the check standard cuvettes used with the apparatus are 10.0 mm (width) by 15.0 mm (depth) by 38.0 mm (height), inside dimensions, crown glass cuvettes having four optically clear walls that contain a certified solid semi-transparent material (optional); (6) the crown glass cuvettes used with the apparatus are has inside dimensions of 10.0 mm (width) by 15.0 mm (depth) by 38 mm (height), and are optically clear on all four sides; (7) the cuvette dimensions are within ±0.1 mm tolerances; and (8) the apparatus includes a temperature-controlled bath of suitable dimensions and capable of controlling the sample container temperature within ±0.5° C. of the desired temperature for laboratory tests that require measurements to be made at a specific temperatures.

Samples are obtained in accordance with ASTM D4057 or D4177. The apparatus is prepared and calibrated in accordance with the procedures set forth in ASTM D8148-17. A conditioned sample is then analyzed in accordance with the procedures set forth in ASTM D8148-17.

Certain Embodiments

Certain non-limiting, exemplary embodiments will now be set forth.

Embodiment 1. An apparatus for measuring optical properties of liquid samples, the apparatus comprising: a sample chamber; a spectrometer optically coupled with the sample chamber; a first photodetector optically coupled with the sample chamber; a second photodetector optically coupled with the sample chamber; a first source of electromagnetic radiation positioned relative to the sample chamber to direct electromagnetic radiation through the sample chamber along a first optical path and into the spectrometer for measurement of color; a second source of electromagnetic radiation positioned relative to the sample chamber to direct electromagnetic radiation through the sample chamber and into the first photodetector and the second photodetector for measurement of haze; wherein the first photodetector and the second source of electromagnetic radiation are positioned relative to one another and to the sample chamber to define a first detection channel wherein electromagnetic radiation from the second source of electromagnetic radiation passes through the sample chamber into the first photodetector to measure transmittance of the electromagnetic radiation through the sample chamber; and wherein the second photodetector and the second source of electromagnetic radiation are positioned relative to one another and to the sample chamber to define a second detection channel wherein electromagnetic radiation from the second source of electromagnetic radiation is scattered within the sample chamber and into the second photodetector to measure scatter of the electromagnetic radiation within the sample chamber.

Embodiment 2. The apparatus of Embodiment 1, wherein the second source of electromagnetic radiation includes a near-infrared light.

Embodiment 3. The apparatus of Embodiment 1 or 2, wherein the second source of electromagnetic radiation emits electromagnetic radiation within the wavelength range of from 800 nm to 880 nm.

Embodiment 4. The apparatus of any of Embodiments 1-3, further comprising a refractive surface positioned in the path of the electromagnetic radiation from the second source between the second source and the sample chamber.

Embodiment 5. The apparatus of any of Embodiments 1-4, further comprising a tandem aperture positioned in the path of the electromagnetic radiation from the second source between the first photodetector and the sample chamber.

Embodiment 6. The apparatus of any of Embodiments 1-5, wherein the second photodetector includes a nephelometer.

Embodiment 7. The apparatus of any of Embodiments 1-6, further comprising a lens positioned in the path of the electromagnetic radiation from the second source between the second photodetector and the sample chamber.

Embodiment 8. The apparatus of any of Embodiments 1-7, further comprising a temperature sensor positioned within the chamber to measure the temperature of liquid samples.

Embodiment 9. The apparatus of Embodiment 8, wherein the apparatus is configured to measure haze only when a liquid sample is at a temperature that is within a preset temperature range.

Embodiment 10. The apparatus of any of Embodiments 1-9, wherein haze is measured in accordance with ASTM D8148-17.

Embodiment 11. The apparatus of any of Embodiments 1-10, further comprising a computer in data communication with the spectrometer, the first photodetector, and the second photodetector, wherein the computer receives measurement data from the spectrometer, the first photodetector, and the second photodetector, the computer comprising instructions to analyze the measurement data and form color data and haze data.

Embodiment 12. The apparatus of Embodiment 11, wherein the haze data includes an instrument haze rating that is a whole number ranging from 1 to 6 and a haze clarity index of from 50 to 100.

Embodiment 13. The apparatus of Embodiment 12, wherein the haze data is in the form of a bar graph of the haze clarity index, a graph of the haze clarity index versus liquid sample temperature, a graph of liquid sample temperature versus the instrument haze rating, or combinations thereof.

Embodiment 14. The apparatus of any of Embodiments 1-13, wherein the first source of electromagnetic radiation emits electromagnetic radiation within a wavelength range of from 380 nm to 780 nm.

Embodiment 15. The apparatus of any of Embodiments 1-14, wherein the first source of electromagnetic radiation includes a light source, a flux collector positioned to receive light from the light source, a cylindrical diffuser positioned to receive light from the flux collector, and illuminating formatting optics positioned to receive light from the cylindrical diffuser.

Embodiment 16. The apparatus of any of Embodiments 1-15, further comprising a collection lens positioned within the path of electromagnetic radiation emitted from the first source, between the sample chamber and the spectrometer.

Embodiment 17. The apparatus of Embodiment 16, further comprising a chamber window positioned within the path of electromagnetic radiation emitted from the first source, between the first source and the collection lens.

Embodiment 18. The apparatus of any of Embodiments 1-17, wherein the color is measured in accordance with ASTM D156-15, ASTM D1500-12(2017), ASTM D6045-12(2017), ASTM D5386-16, or ASTM D1209-05(2011).

Embodiment 19. The apparatus of any of Embodiments 1-18, wherein the sample chamber accommodates multiple, different sizes of cuvettes.

Embodiment 20. The apparatus of any of Embodiments 1-29, further comprising a sensor positioned within the sample chamber to detect the presence of cuvettes installed within the sample chamber, the size of cuvettes installed within the sample chamber, the position of cuvettes installed within the sample chamber, or combinations thereof.

Embodiment 21. The apparatus of Embodiment 20, wherein the sensor includes a plunger sensor, a proximity sensor, or combinations thereof.

Embodiment 22. The apparatus of any of Embodiments 1-21, wherein the apparatus is programmed to perform a series of measurements of haze, color, or both over a period of time corresponding to settling of a liquid sample from an agitated state to a settled, non-agitated state.

Embodiment 23. The apparatus of any of Embodiments 1-22, further comprising a lid coupled with the sample chamber, wherein the lid is articulable into a closed position and an open position, and wherein the apparatus includes a sensor positioned to sense if the lid is in the closed position or the open position.

Embodiment 24. The apparatus of any of Embodiments 1-24, further comprising at least one self-alignment feature tailored to move or facilitate movement of a cuvette into a proper position within the sample chamber.

Embodiment 25. The apparatus of Embodiment 24, wherein the at least one self-alignment comprises a force applicator positioned on a lid coupled with the sample chamber, wherein the lid is articulable into a closed position and an open position, and wherein the force applicator is positioned to engage with a cuvette positioned within the chamber when the lid is in the closed position.

Embodiment 26. The apparatus of Embodiment 25, wherein the force applicator comprises a clamp.

Embodiment 27. The apparatus of Embodiment 25, wherein the force applicator comprises a ball engaged with a spring.

Embodiment 28. A method for measuring optical properties of liquid samples, the method comprising: inserting a first sample of a liquid into a sample chamber of an apparatus; directing electromagnetic radiation through the first sample and to a spectrometer to measure a color of the liquid; inserting a second sample of the liquid into the sample chamber of the apparatus; and directing electromagnetic radiation through the second sample and to photodetectors to measure a haze of the liquid.

Embodiment 29. The method of Embodiment 28, wherein the liquid comprises a petroleum-based liquid.

Embodiment 30. The method of Embodiment 29, wherein the petroleum-based liquid includes a fuel or a lubricant.

Embodiment 31. The method of Embodiment 29, wherein the petroleum-based liquid includes a middle distillate.

Embodiment 32. The method of Embodiment 31, wherein the middle distillate includes heating oil, distillate fuel oil, gas oil, lighting oil, or cooking oil.

Embodiment 33. The method of Embodiment 31, wherein the middle distillate includes kerosene, jet fuel, diesel fuel, or marine bunker fuel.

Embodiment 34. The method of Embodiment 31, wherein the middle distillate includes from eleven to eighteen carbons atoms in each molecule thereof.

Embodiment 35. The method of any of Embodiments 28-34, wherein the liquid includes a contaminate.

Embodiment 36. The method of Embodiment 35, wherein the contaminate includes water, solid particulate, or combinations thereof.

Embodiment 37. The method of any of Embodiments 28-36, wherein the haze is measured in accordance with ASTM D8148-17.

Embodiment 38. The method of any of Embodiments 28-37, wherein measuring the haze includes determining instrument haze rating and a haze clarity index for the liquid sample, wherein the instrument haze rating is a whole-number ranging from 1 to 6, and wherein the haze clarity index ranges from 50 to 100.

Embodiment 39. The method of Embodiment 38, further comprising presenting results of the haze measurement in the form of a bar graph of haze clarity index, a graph of haze clarity index versus the temperature of the liquid sample, a graph of the temperature of the liquid sample versus the instrument haze rating, or combinations thereof.

Embodiment 40. The method of any of Embodiments 28-39, wherein the electromagnetic radiation transmitted through the liquid to measure haze is within the wavelength range of from 800 nm to 880 nm.

Embodiment 41. The method of any of Embodiments 28-40, wherein the haze is measured by preforming a single measurement of the liquid; multiple, prompted measurements of the liquid; or multiple, pre-timed measurements of the liquid.

Embodiment 42. The method of any of Embodiments 28-41, further comprising, prior to inserting the second sample into the sample chamber, agitating the second sample.

Embodiment 43. The method of any of Embodiments 28-42, wherein the method includes performing a series of multiple haze measurements of the second sample over a period of time.

Embodiment 44. The method of any of Embodiments 28-43, further comprising measuring the temperature of the liquid sample before measuring the haze of the liquid sample, measuring the temperature of the liquid sample concurrently with measurement of the haze of the liquid sample, or combinations thereof.

Embodiment 45. The method of Embodiment 44, further comprising measuring the haze of the liquid sample when the liquid sample is at a predetermined temperature or within a predetermined temperature range.

Embodiment 46. The method of Embodiment 45, further comprising, prior to measuring the haze of the liquid sample, heating or cooling the liquid sample.

Embodiment 47. The method of any of Embodiments 28-46, wherein directing electromagnetic radiation through the second sample to measure the haze of the liquid includes, prior to the electromagnetic radiation passing through the liquid, directing the electromagnetic radiation through a refractive surface to control divergence.

Embodiment 48. The method of any of Embodiments 28-47, wherein measuring the haze of the liquid sample includes detecting electromagnetic radiation that is transmitted through the liquid along a first detection channel to measure loss of light through liquid, and detecting electromagnetic radiation that is scattered within the liquid along a second detection channel to measure scatter of light through liquid.

Embodiment 49. The method of Embodiment 48, wherein the electromagnetic radiation is detected by a first photodetector along the first detection channel, and by a second photodetector along the second detection channel.

Embodiment 50. The method of Embodiment 49, further comprising directing the electromagnetic radiation exiting the liquid along the first channel through a tandem aperture prior to detection by the first photoreactor.

Embodiment 51. The method of Embodiment 49, wherein the second photodetector is a nephelometer, and wherein the method includes directing the electromagnetic radiation exiting the liquid along the second channel through a lens prior to detection by the second photoreactor.

Embodiment 52. The method of any of Embodiments 28-51, further comprising determining a level of suspended water and solid particulate contamination present in the liquid sample.

Embodiment 53. The method of any of Embodiments 28-52, wherein the color is measured in accordance with ASTM D156-15, ASTM D1500-12(2017), ASTM D6045-12(2017), ASTM D5386-16, or ASTM D1209-05(2011).

Embodiment 54. The method of any of Embodiments 28-53, wherein the electromagnetic radiation transmitted through the liquid to determine the color is within the wavelength range of from 380 nm to 780 nm.

Embodiment 55. The method of any of Embodiments 28-54, wherein directing electromagnetic radiation through the liquid to measure the color of the liquid includes directing the electromagnetic radiation from a source to a flux collector, from the flux collector to a cylindrical diffuser, from the cylindrical diffuser to illumination formatting optics, and from the illumination formatting optics into the liquid sample.

Embodiment 56. The method of Embodiment 55, wherein the illumination formatting optic collimates the electromagnetic radiation.

Embodiment 57. The method of any of Embodiments 28-56, wherein directing electromagnetic radiation through the liquid to measure the color of the liquid includes directing the electromagnetic radiation from the liquid through a collection lens, and from the collection lens to a spectrometer.

Embodiment 58. The method of any of Embodiments 28-57, wherein the liquid samples are contained within cuvettes, the method further comprising aligning the cuvettes within the sample chamber using a self-alignment feature tailored to move or facilitate movement of the cuvettes containing the liquid sample into position within the sample chamber.

Embodiment 59. The method of any of Embodiments 28-58, wherein the liquid samples are contained within cuvettes, the method further comprising sensing the size of the cuvettes inserted into the sample chamber, sensing the presence of cuvettes inserted into the sample chamber, sensing the position of cuvettes inserted into the sample chamber, or combinations thereof.

Embodiment 60. The method of Embodiment 59, wherein the cuvettes are sensed with a plunger sensor or proximity sensor.

Embodiment 61. The method of any of Embodiments 28-60, wherein a series of measurements of the color, haze, or combinations thereof are taken of the liquid while the liquid settles from an agitated state to a settled, non-agitated state.

Embodiment 62. A liquid measured in accordance with the method of any of Embodiments 28-61.

Although the present embodiments and advantages have been described in detail, it should be understood that various changes, substitutions and alterations can be made herein without departing from the spirit and scope of the disclosure. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. An apparatus for measuring optical properties of liquid samples, the apparatus comprising:
    a sample chamber;
    a spectrometer optically coupled with the sample chamber;
    a first photodetector optically coupled with the sample chamber;
    a second photodetector optically coupled with the sample chamber;
    a first source of electromagnetic radiation positioned relative to the sample chamber to direct electromagnetic radiation through the sample chamber along a first optical path and into the spectrometer for measurement of color;
    a second source of electromagnetic radiation positioned relative to the sample chamber to direct electromagnetic radiation through the sample chamber and into the first photodetector and the second photodetector for determination of haze data from measured transmittance and measured scatter, the haze data comprising an instrument haze rating and a haze clarity index;
    wherein the first photodetector and the second source of electromagnetic radiation are positioned relative to one another and to the sample chamber to define a first detection channel wherein electromagnetic radiation from the second source of electromagnetic radiation passes through the sample chamber into the first photodetector to measure transmittance of the electromagnetic radiation through the sample chamber; and
    wherein the second photodetector and the second source of electromagnetic radiation are positioned relative to one another and to the sample chamber to define a second detection channel wherein electromagnetic radiation from the second source of electromagnetic radiation is scattered within the sample chamber and into the second photodetector to measure scatter of the electromagnetic radiation within the sample chamber.

2. The apparatus of claim 1, further comprising a temperature sensor positioned within the chamber to measure the temperature of liquid samples, wherein the apparatus is configured to measure haze only when a liquid sample is at a temperature that is within a preset temperature range.

3. The apparatus of claim 1, further comprising a computer in data communication with the spectrometer, the first photodetector, and the second photodetector, wherein the computer receives measurement data from the spectrometer, the first photodetector, and the second photodetector, the computer comprising instructions to analyze the measurement data and form color data and the haze data, wherein the haze data includes an instrument haze rating that is a whole number ranging from 1 to 6 and a haze clarity index of from 50 to 100.

4. The apparatus of claim 1, wherein the sample chamber accommodates multiple, different sizes of cuvettes.

5. The apparatus of claim 1, further comprising a sensor positioned within the sample chamber to detect the presence of cuvettes installed within the sample chamber, the size of cuvettes installed within the sample chamber, the position of cuvettes installed within the sample chamber, or combinations thereof.

6. The apparatus of claim 5, wherein the sensor comprises a plunger sensor, a proximity sensor, or combinations thereof.

7. The apparatus of claim 1, further comprising a lid coupled with the sample chamber, wherein the lid is articulable into a closed position and an open position, and wherein the apparatus includes a sensor positioned to sense if the lid is in the closed position or the open position.

8. The apparatus of claim 1, further comprising at least one self-alignment feature tailored to move or facilitate movement of a cuvette into a proper position within the sample chamber.

9. The apparatus of claim 8, wherein the at least one self-alignment comprises a force applicator positioned on a lid coupled with the sample chamber, wherein the lid is articulable into a closed position and an open position, and wherein the force applicator is positioned to engage with a cuvette positioned within the chamber when the lid is in the closed position.

10. The apparatus of claim 9, wherein the force applicator comprises a clamp.

11. The apparatus of claim 9, wherein the force applicator comprises a ball engaged with a spring.

12. The apparatus of claim 1, wherein the haze data comprises a bar graph of the haze clarity index, a graph of the haze clarity index versus liquid sample temperature, a graph of liquid sample temperature versus the instrument haze rating, or combinations thereof.

13. The apparatus of claim 1, wherein the sample chamber accommodates a first cuvette within a first volume of the sample chamber and a second cuvette within a second volume of the sample chamber, and wherein the first volume is discrete from the second volume.

14. The apparatus of claim 1, wherein the haze data is determined in accordance with ASTM D8148, and wherein the instrument haze rating is a whole number ranging from 1 to 6 and the haze clarity index ranges from 50 to 100.

15. A method for measuring optical properties of liquid samples, the method comprising:
inserting a first sample of a liquid into a sample chamber of an apparatus;
directing electromagnetic radiation through the first sample and to a spectrometer to measure a color of the liquid;
inserting a second sample of the liquid into the sample chamber of the apparatus;
directing electromagnetic radiation through the second sample and to first photodetector to measure transmittance of electromagnetic radiation through the liquid and to a second photodetector to measure scatter of electromagnetic radiation through the liquid to determine a haze of the liquid, wherein determining the haze includes determining an instrument haze rating and a haze clarity index for the liquid, wherein the instrument haze rating is a whole-number ranging from 1 to 6, and wherein the haze clarity index ranges from 50 to 100; and
determining a level of contaminate present in the liquid.

16. The method of claim 15, wherein the liquid comprises a petroleum-based liquid.

17. The method of claim 16, wherein the petroleum-based liquid includes a fuel or a lubricant.

18. The method of claim 15, wherein the electromagnetic radiation transmitted through the liquid to measure haze is within the wavelength range of from 800 nm to 880 nm, and wherein the electromagnetic radiation transmitted through the liquid to determine the color is within the wavelength range of from 380 nm to 780 nm.

19. The method of claim 15, further comprising, prior to inserting the second sample into the sample chamber, agitating the second sample.

20. The method of claim 15, further comprising measuring the temperature of the liquid sample before measuring the haze of the liquid sample, measuring the temperature of the liquid sample concurrently with measurement of the haze of the liquid sample, or combinations thereof; and
measuring the haze of the liquid sample when the liquid sample is at a predetermined temperature or within a predetermined temperature range.

21. The method of claim 20, further comprising, prior to measuring the haze of the liquid sample, heating or cooling the liquid sample.

22. The method of claim 15, wherein measuring the haze of the liquid sample includes detecting electromagnetic radiation that is transmitted through the liquid along a first detection channel to measure loss of light through liquid, and detecting electromagnetic radiation that is scattered within the liquid along a second detection channel to measure scatter of light through liquid.

23. The method of claim 15, wherein a series of measurements of the color, haze, or combinations thereof are taken of the liquid while the liquid settles from an agitated state to a settled, non-agitated state.

24. The method of claim 15, wherein the haze is determined in accordance with ASTM D8148.

25. An apparatus for measuring optical properties of liquid fuel, the apparatus comprising:
a sample chamber, the sample chamber having a first volume for receipt of a first sample of the liquid fuel and a second volume for receipt of a second sample of the liquid fuel, wherein the first volume is discrete from the second volume;
a spectrometer optically coupled with the sample chamber;
a first source of electromagnetic radiation positioned relative to the sample chamber to direct electromagnetic radiation through the second volume of the sample chamber along a first optical path and into the spectrometer for measurement of color;
a first photodetector optically coupled with the sample chamber;
a second photodetector optically coupled with the sample chamber;
a second source of electromagnetic radiation positioned relative to the sample chamber to direct electromagnetic radiation through the first volume of the sample chamber and into the first and second photodetectors to determine haze data from measured transmittance and measured scatter, the haze data comprising an instrument haze rating and a haze clarity index as determined in accordance with ASTM D8148, wherein the instrument haze rating is a whole number ranging from 1 to 6 and the haze clarity index ranges from 50 to 100;
wherein the first photodetector and the second source of electromagnetic radiation are positioned relative to one another and to the sample chamber to define a first detection channel wherein electromagnetic radiation from the second source of electromagnetic radiation passes through the first volume of the sample chamber into the first photodetector to measure transmittance of the electromagnetic radiation through the sample chamber; and wherein the second photodetector and the second source of electromagnetic radiation are positioned relative to one another and to the sample chamber to define a second detection channel wherein electromagnetic radiation from the second source of electromagnetic radiation is scattered within the first volume of the sample chamber and into the second photodetector to measure scatter of the electromagnetic radiation within the sample chamber.

* * * * *